United States Patent [19]

Gray et al.

[11] Patent Number: 5,358,663
[45] Date of Patent: Oct. 25, 1994

[54] LATERALLY CYANO- AND FLUORO-SUBSTITUTED TERPHENYLS

[75] Inventors: George W. Gray, Cottingham; David Lacey; Michael Hird, both of Hull; Kenneth J. Toyne, Hull, all of England

[73] Assignee: The Secretary of State for Defence in her Britannic Majesty'3 s Government of U.K. of Gt. Britain and N. Ireland, United Kingdom

[21] Appl. No.: 946,773
[22] PCT Filed: Oct. 19, 1988
[86] PCT No.: PCT/GB88/00880
§ 371 Date: Apr. 11, 1990
§ 102(e) Date: Apr. 11, 1990
[87] PCT Pub. No.: WO89/03821
PCT Pub. Date: May 5, 1989

Related U.S. Application Data

[63] Continuation of Ser. No. 469,486, Apr. 11, 1990, abandoned.

[30] Foreign Application Priority Data

Oct. 19, 1987 [GB] United Kingdom ............... 8724458

[51] Int. Cl.$^5$ .................... C09K 19/12; C09K 19/06; C09K 19/52; G02F 1/13
[52] U.S. Cl. .................... 252/299.660; 252/299.6; 252/299.01
[58] Field of Search ........... 252/299.66, 299.6, 299.01; 359/104

[56] References Cited

U.S. PATENT DOCUMENTS

| | | | |
|---|---|---|---|
| 4,478,740 | 10/1984 | Eidenschink et al. | 252/299.62 |
| 4,510,069 | 4/1985 | Eidenschink et al. | 252/299.61 |
| 4,536,321 | 8/1985 | Sugimori et al. | 568/331 X |
| 4,594,465 | 6/1986 | Chan et al. | 252/299.62 X |
| 4,614,608 | 9/1986 | LeBarny et al. | 560/62 X |
| 4,670,182 | 6/1987 | Fujita et al. | 252/299.61 |
| 4,696,549 | 9/1987 | Chan et al. | 350/350 R |
| 4,709,030 | 11/1987 | Petrzilka et al. | 544/242 |
| 4,728,458 | 3/1988 | Higuchi et al. | 252/299.65 |
| 4,776,975 | 10/1988 | Sawada et al. | 252/299.61 |
| 4,822,519 | 4/1989 | Saito et al. | 252/299.61 |
| 4,846,998 | 7/1989 | Pohl et al. | 252/299.63 |
| 4,867,903 | 8/1989 | Nohira et al. | 252/299.61 |
| 4,871,469 | 10/1989 | Reiffenrath et al. | 252/299.61 |
| 4,871,472 | 10/1989 | Krause et al. | 252/299.65 |
| 4,923,633 | 5/1990 | Gray et al. | 252/299.65 |
| 5,064,569 | 11/1991 | Geelhaar et al. | 252/299.65 |

FOREIGN PATENT DOCUMENTS

| | | | |
|---|---|---|---|
| 0058981 | 9/1982 | European Pat. Off. | 252/299.63 |
| 0064193 | 11/1982 | European Pat. Off. | |
| 0132377 | 1/1985 | European Pat. Off. | |
| 0178847 | 4/1986 | European Pat. Off. | 252/299.63 |
| 0206228 | 12/1986 | European Pat. Off. | 252/299.66 |
| 1468202 | 5/1969 | Fed. Rep. of Germany | 568/331 |
| 2939782 | 4/1981 | Fed. Rep. of Germany | |
| 3533333 | 3/1987 | Fed. Rep. of Germany | |
| 2039937 | 8/1980 | United Kingdom | |
| 2198743 | 6/1988 | United Kingdom | 252/299.66 |

Primary Examiner—Robert L. Stoll
Assistant Examiner—C. Harris
Attorney, Agent, or Firm—Nixon & Vanderhye

[57] ABSTRACT

Laterally cyano-substituted terphenyls of formula (I), wherein $R^1$ and $R^2$ are independently selected from hydrogen or $C_{1-15}$ alkyl, alkoxy, or alkyl or alkoxy in which one or more $CH_2$ groups are replaced by O, COO, OOC, CHX, $CX_2$, CH=CX, CX=CH, CX=CX, where X is fluorine or chlorine. CRCN where R is alkyl, or C≡C or in which a terminal $CH_3$ of the said alkyl or alkoxy chain is replaced by $CF_3$, n is 0 or 1, and the CN and F (if present) substituent are independently located in any of the available substitution positions. Liquid crystal materials containing these terphenyls are also described.

13 Claims, 12 Drawing Sheets

Routes A1 and A2

R, R¹, R² = alkyl or alkoxy

Fig.2.
Routes B1 and B2
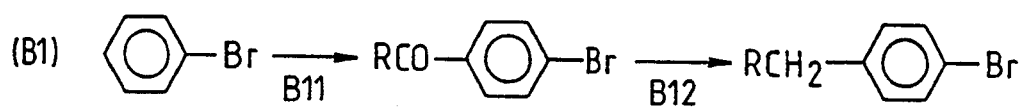
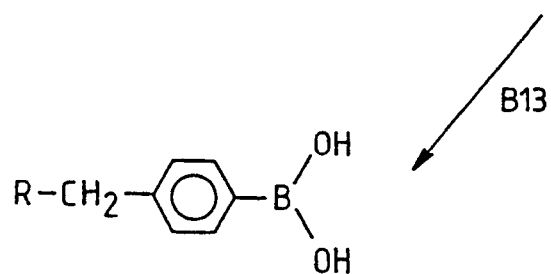
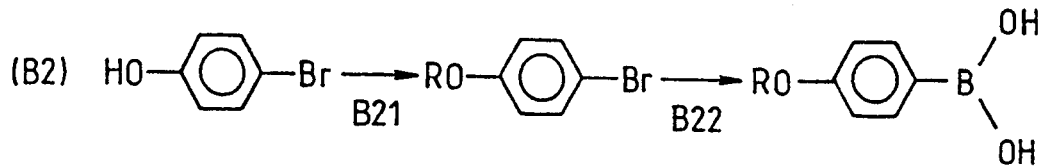
R = alkyl

Route C1

R¹ = alkyl or alkoxy

R = alkyl one of a or b = 1
"    "  "  "  " = 0

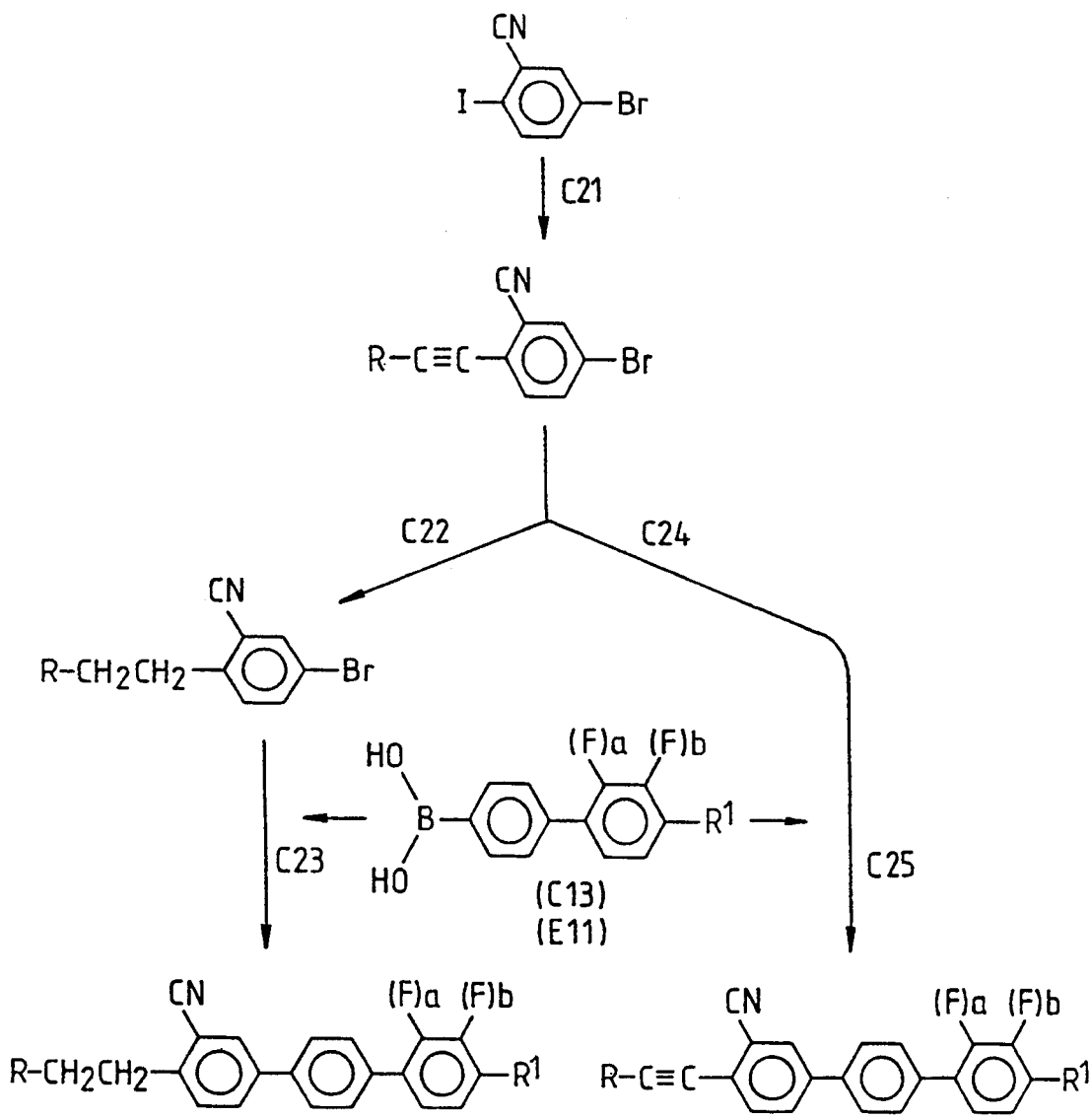
Fig. 4.  Route C2

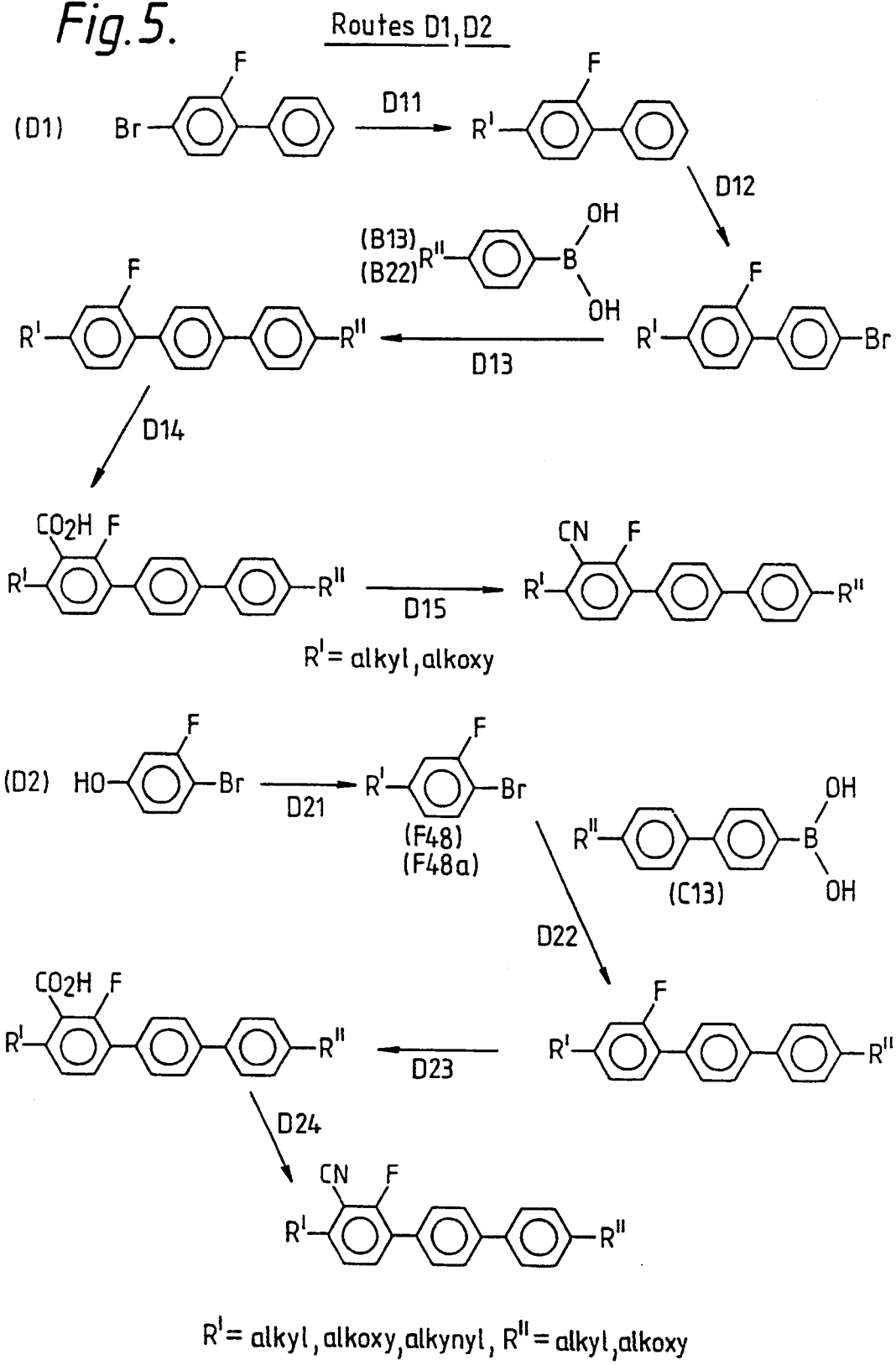

Fig.6. Routes D3, D4
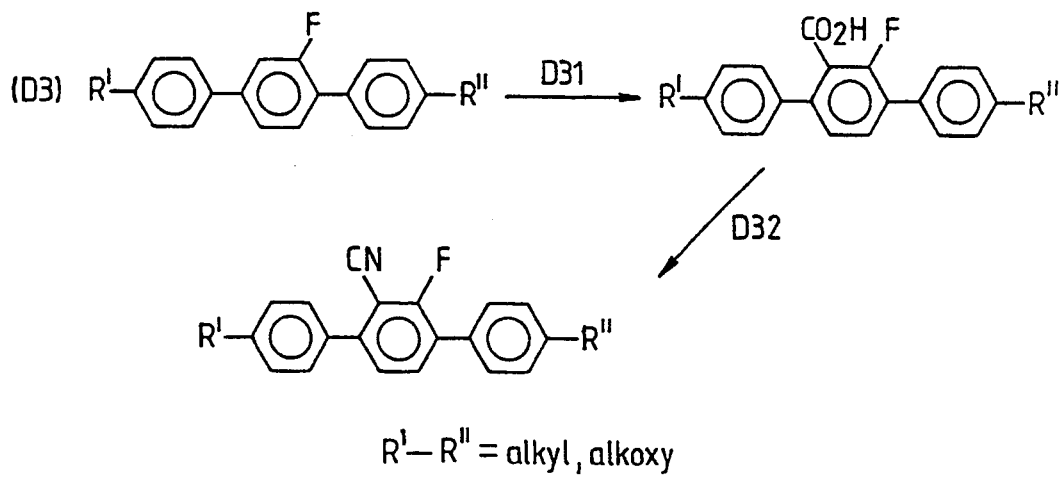
R' — R" = alkyl, alkoxy
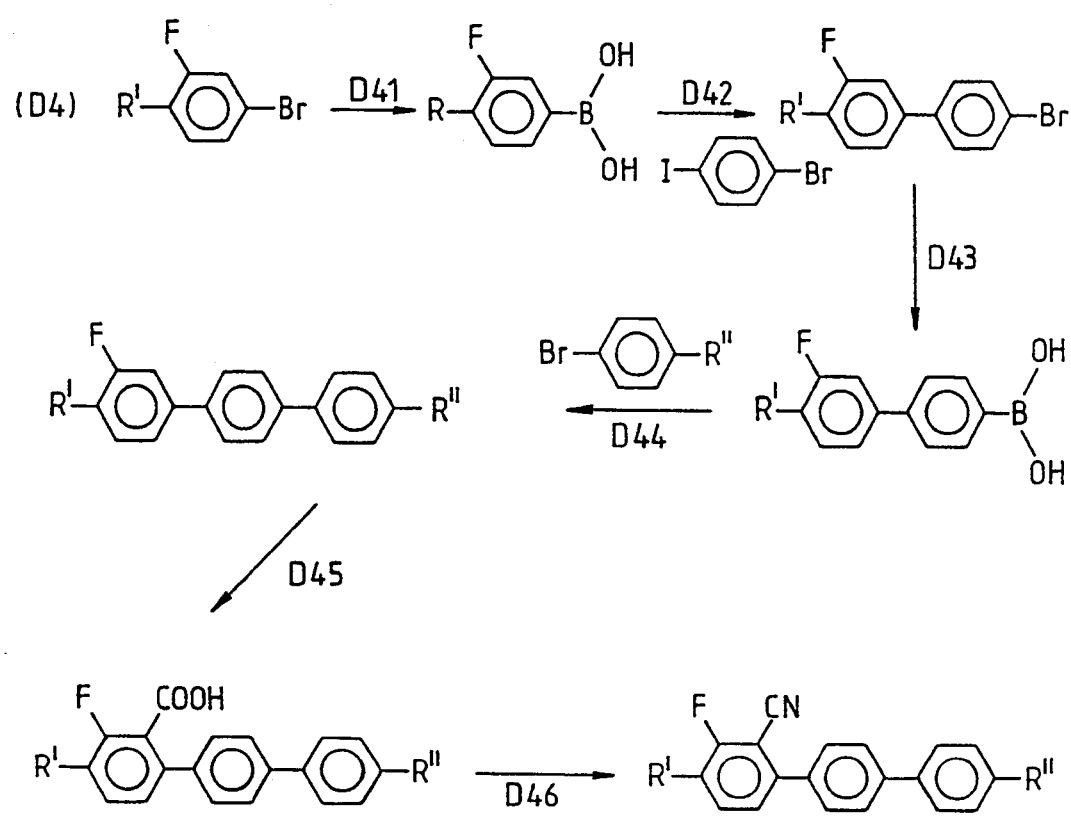
R', R" = alkyl, alkoxy

*Fig.7.*  Route E1
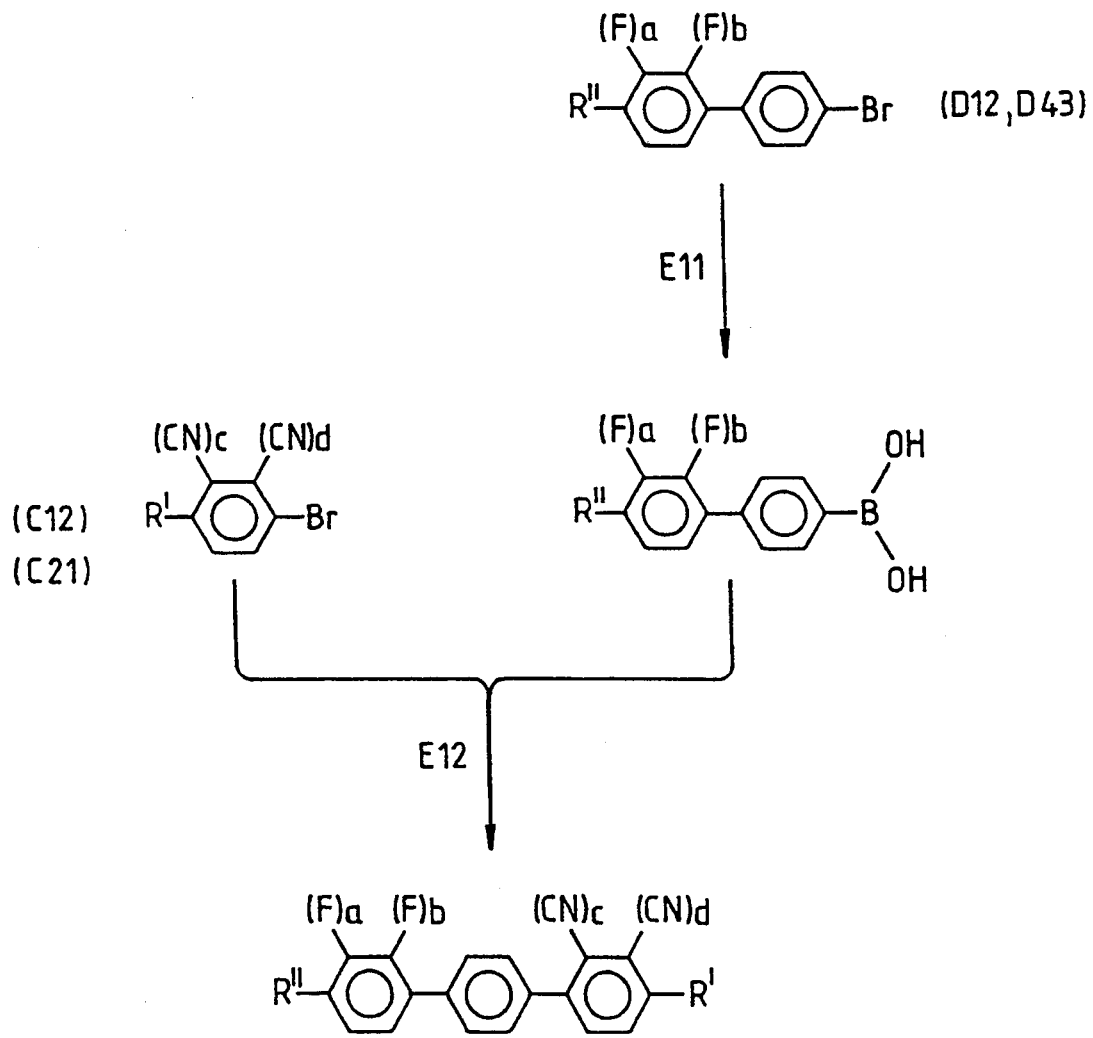
R' = alkyl, alkoxy, alkynyl
R" = alkyl, alkoxy
One of a,b=1, the other=0
One of c,d=1, the other=0

Fig.8. Route E2
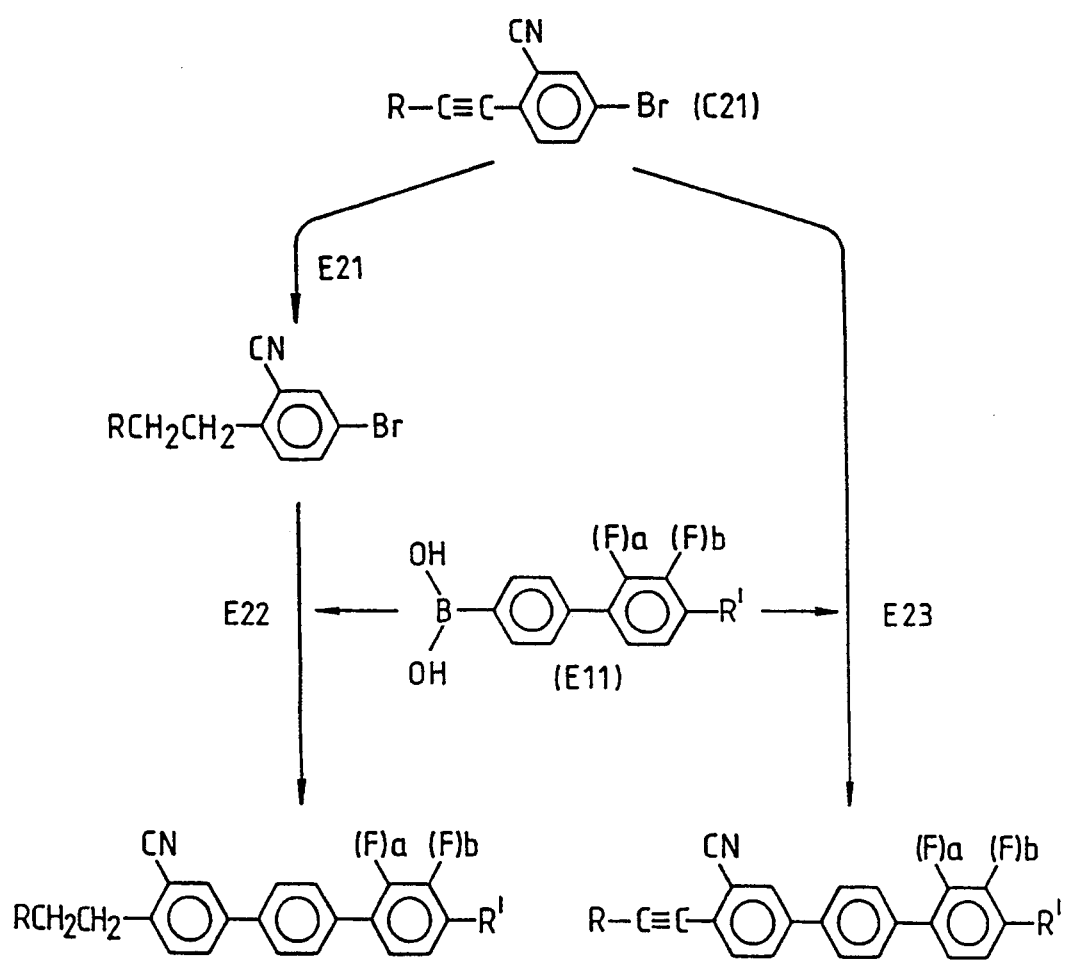
R = alkyl
R' = alkoxy, alkyl
One of a,b=1 the other=0

Routes F1, F2

Route F3

Route F4  Fig.11.

LATERALLY CYANO- AND FLUORO-SUBSTITUTED TERPHENYLS

This is a continuation application Ser. No. 07/469,486, filed Apr. 11, 1990, now abandoned.

This invention relates to laterally cyano- substituted terphenyls, in particular to those which may be used as constituents of liquid crystal mixtures. The invention also relates to such mixtures containing these terphenyls and to electro-optic devices which use them.

BACKGROUND OF THE INVENTION

Liquid crystal materials are well known, and are commonly used in electro-optical devices such as watches, calculators, displays etc. Such materials are of two general types. There are those which use the electro-optical properties of the nematic (N) phase, such as the electrically controlled birefringence (ECB) effect, as described in M. F. Schieckel and K. Fahrenshon, "Defomation of nematic liquid crystals with vertical orientation in electrical fields". Appl Phys Left (1971), 19, 3912. There are also those which use the electrooptical properties manifested by smectic phases. Examples of the latter include the ferroelectric effect manifested by certain chiral tilted smectic phases, see for example N A Clark and S T Lagerwall Appl-Phys Left (1980) 36, 899 which offers the advantages of high speed and bistable properties. The chiral smectic C, F and I phases ($S_C^*$ $S_F^*$ and $S_I^*$I (the asterisk denoting chirality) are generally most favoured for such user the $S_C^*$ being preferred because of its lower viscosity. Another electro-optical effect in smectic phases is the fast-switching electroclinic effect manifested by smectic A phases ($S_A$).

Nematic and ferroelectric smectic liquid crystal materials have a number of desirable requirements in common, which for example include ease of preparation, chemical and photochemical stability, low viscosity and a broad temperature range over which the useful phases (eg N, $S_C$, $S_F$ or $S_I$) persist. Such materials are generally mixtures of compounds and these requirements are sought in compounds or mixtures thereof intended for use in the materials.

Materials and compounds for use in ECB devices and $S_C^*$ devices have a number of specific desirable requirements. For example for use in ECB devices, compounds and materials should preferably show a high value for the ratio of elastic constants $K_3/K_1$, high values for the optical anisotropy $\Delta n$ and a negative dielectric anisotropy $\Delta E$. Indevices which use the ferroelectric effect in $S_C^*$ materials it is desirable that compounds and mixtures show an $S_A$ phase at a temperature above the range over which the $S_C^*$ phase persists, and that undesirable phases such as $S_B$ do not appear.

A number of compounds are known which show broad $S_C$ phases, among which are the alkyl- or alkoxy-terminated fluoroterphenyls ("FTP's") described in EP-A-0132377, of general formula:

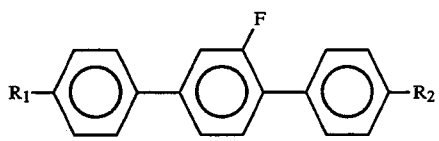

-continued

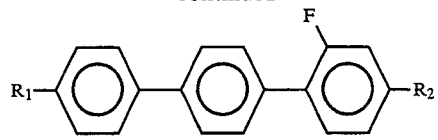

where $R_1$ and $R_2$ are alkyl or alkoxy. Some FTPs and mixtures thereof are known to show broad temperature range $S_C$ phases. This has made them excellent candidates for constituents of ferroelectric smectic mixtures. See for example their use in the mixtures disclosed in PCT/GB 87/0441 and GB 8627107.

It is an object of the present invention to provide novel compounds which may be used as constituents of liquid crystal mixtures, and novel liquid crystal mixtures which incorporate them.

According to this invention novel laterally cyano- substituted terphenyls of general formula I below are provided:

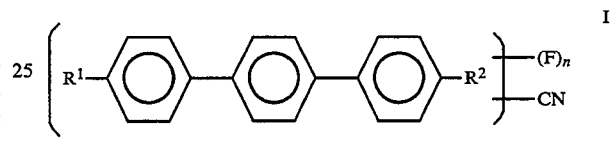

wherein $R^1$ and $R^2$ are independently selected from hydrogen or $C_{1-15}$ alkyl, alkoxy, or alkyl or alkoxy in which one or more $CH_2$ groups are replaced by O, COO, OOC, CHX, $CX_2$, CH=CX, CX=CX, where X ia Fluorine or chlorine, CRCN where R is alkyl, or C≡C, or in which X is terminal. $CH_3$ of the said alkyl or alkoxy chain is replaced by $CF_3$, n is 0 or 1, and the CN and F (if present) substituent are independent located in any of the available substitution positions.

BRIEF DESCRIPTION OF THE DRAWINGS

FIGS. 1–11 illustrate various synthetic routes for preparing the compounds of Formula I retaining the structures of Table 1 to synthesis routes A–F.

DETAILED DESCRIPTION OF THE INVENTION

Figure 1:
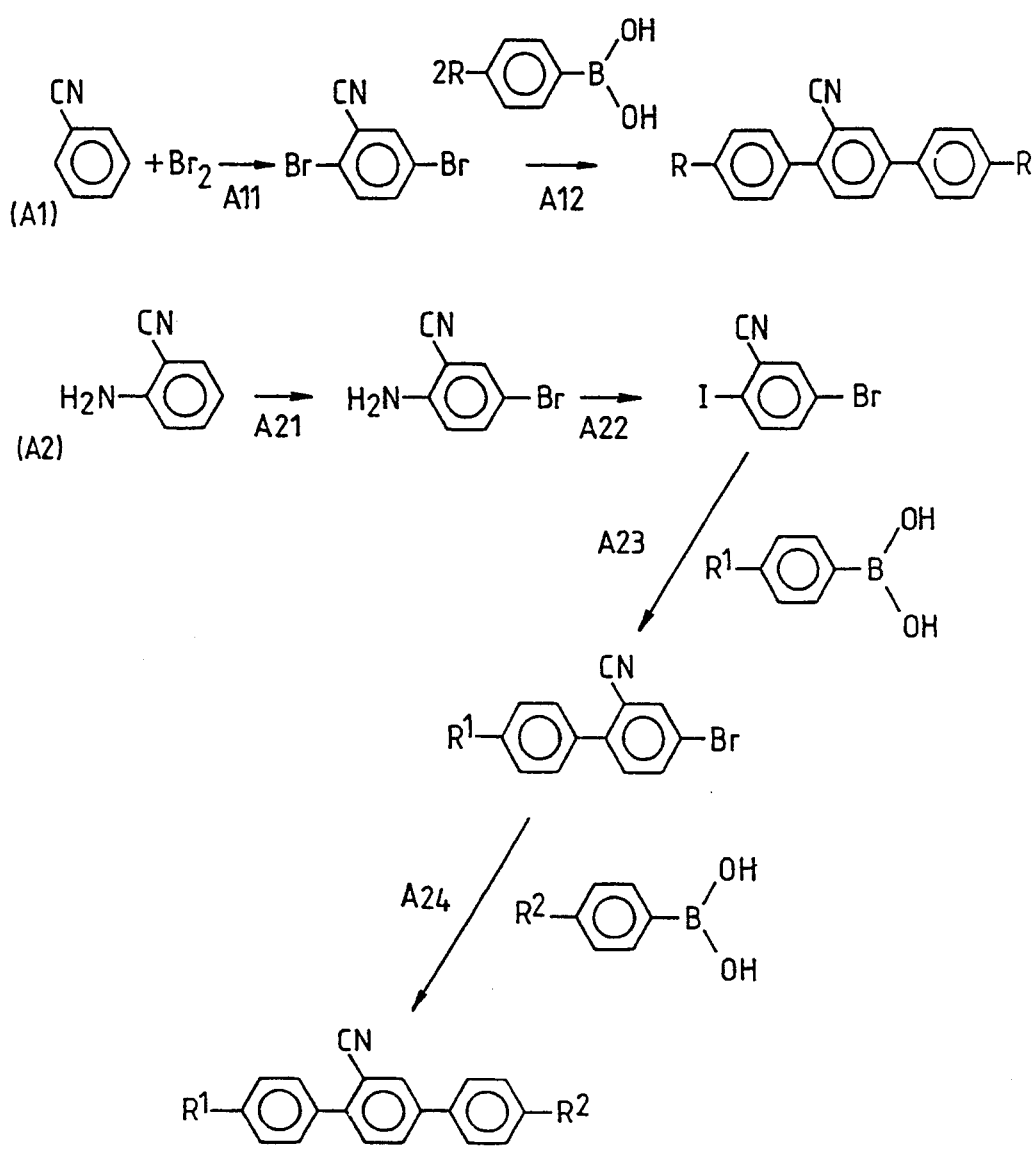
Figure 3:
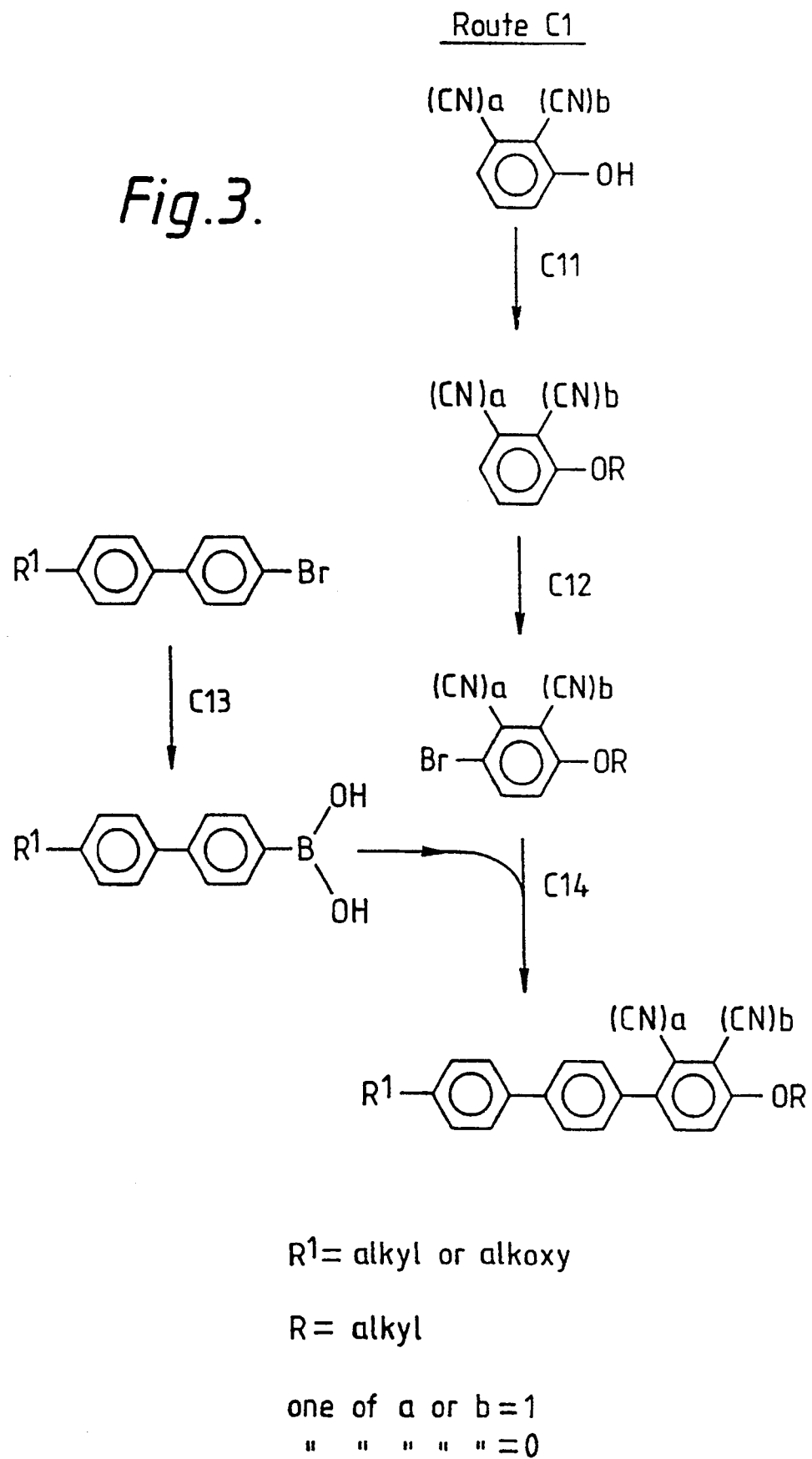
Figure 9:
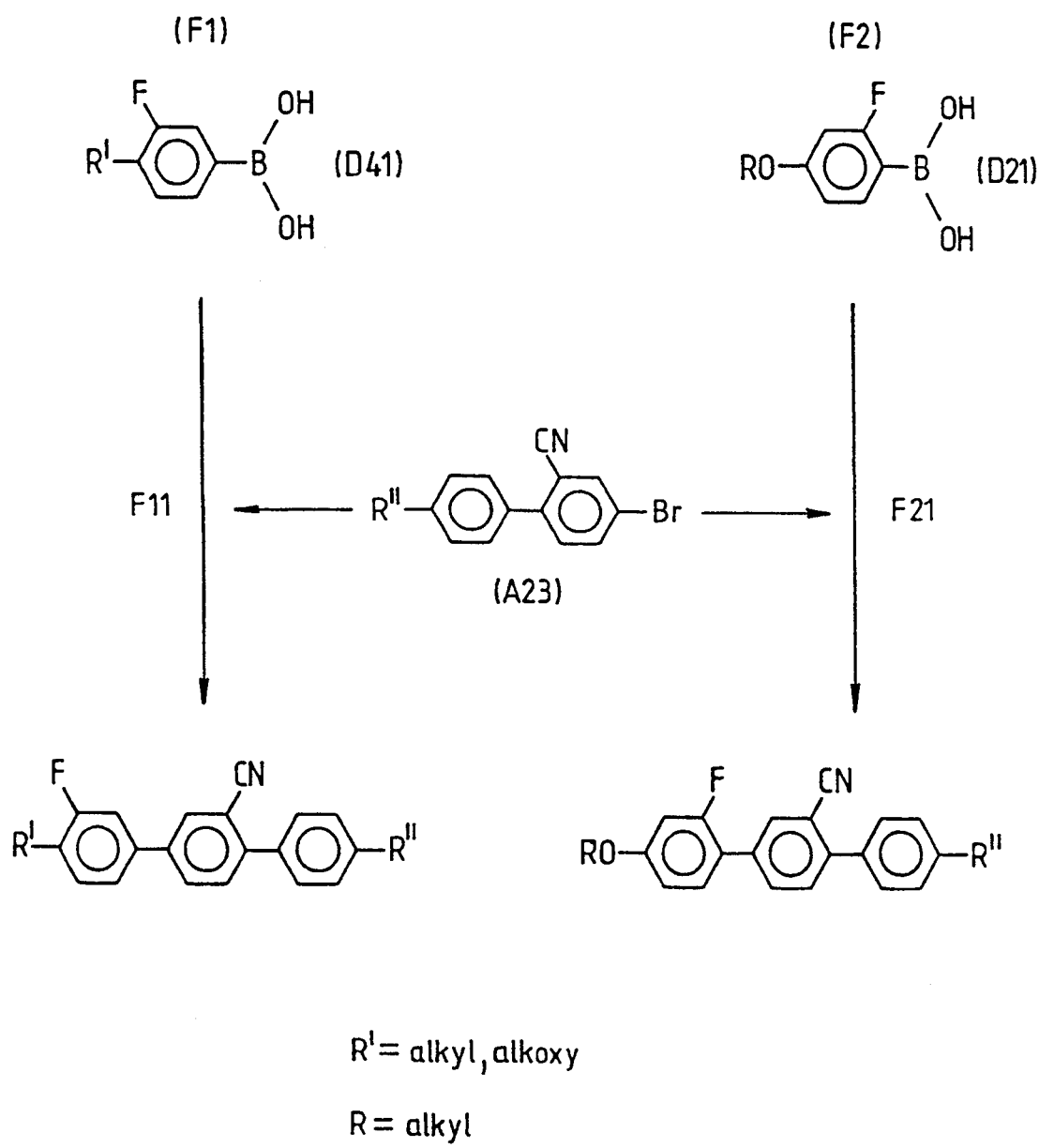
Figure 10:
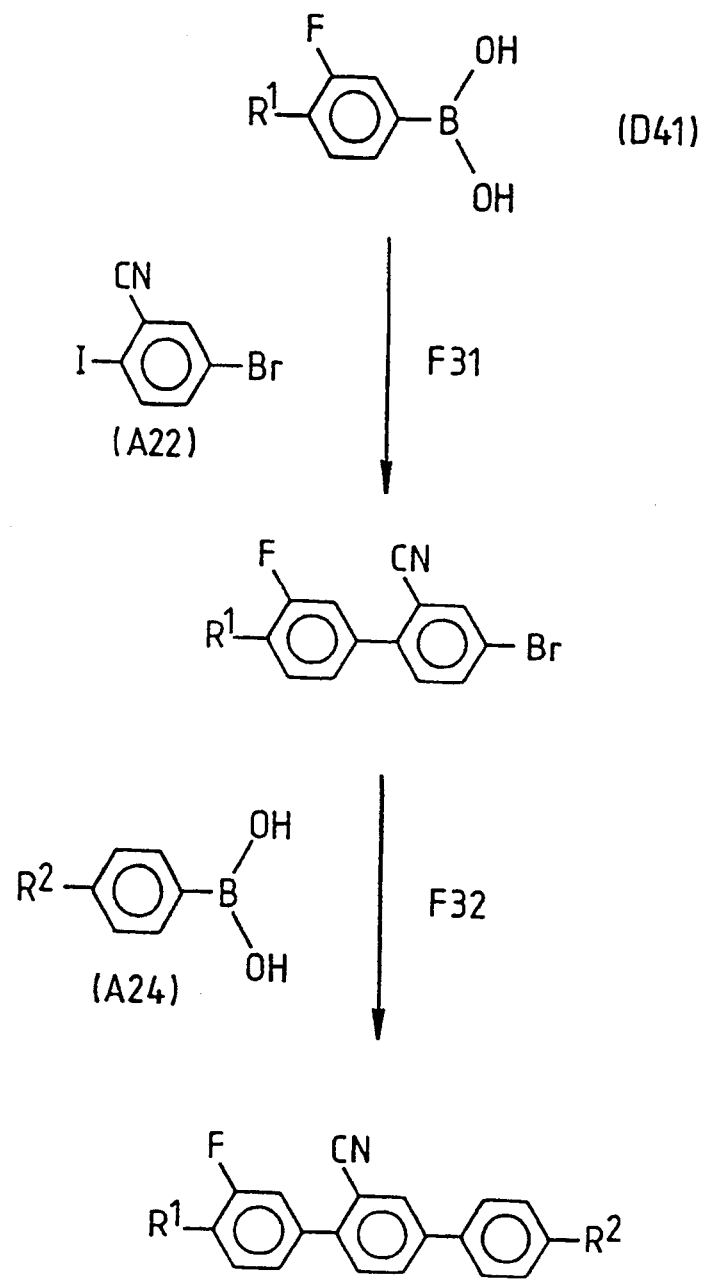
Figure 11:
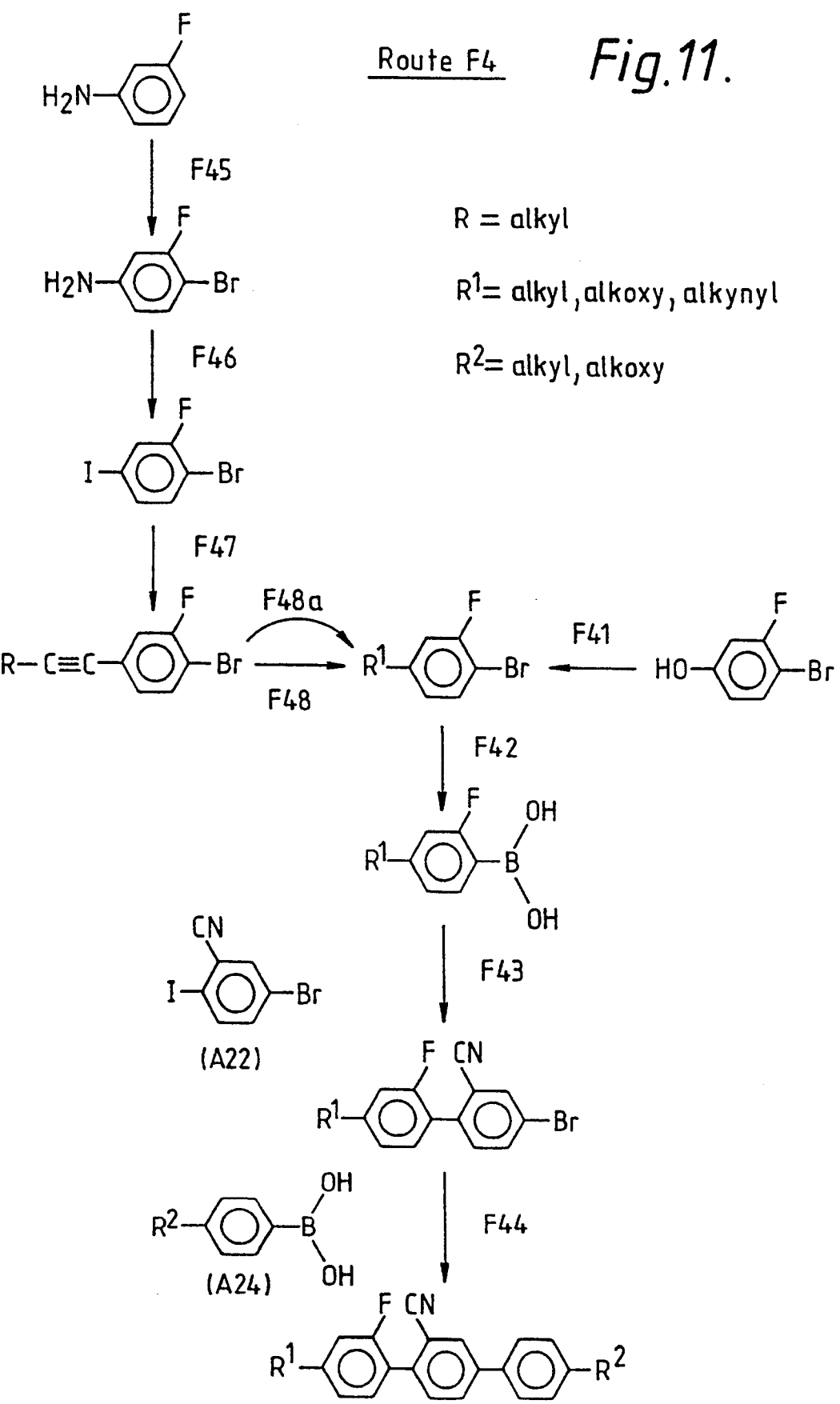

The structural preferences discussed below are based on inter alia on ease of preparation and suitability for use as constituents of liquid crystal mixtures and electro-optical devices which use them.

Preferred structures for terphenyls of formula I are those having a general formula IA below:

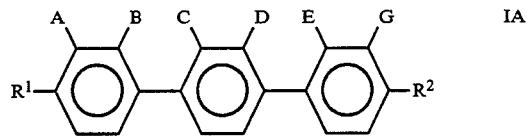

wherein $R^1$ and $R^2$ independently alkyl, alkoxy or alkynyl, and the terphenyl has a substitution pattern selected from any one of the following substitution patterns:
(D=CN), (A=CN), (B=F, G=CN), (A=CN, B=F), (n=CN), (C=CN, D=F), (A=F, G=CN), (A=F, E=CN), (B=F, E=CN), (B=F, D=CN), (A=F, D=CN), (A=F, C=CN), (B=F, C=CN), (A=F, B=CN) the remaining lateral substitution positions being occupied by hydrogen.

The structures included in formula IA are listed below in Table 1.

TABLE 1

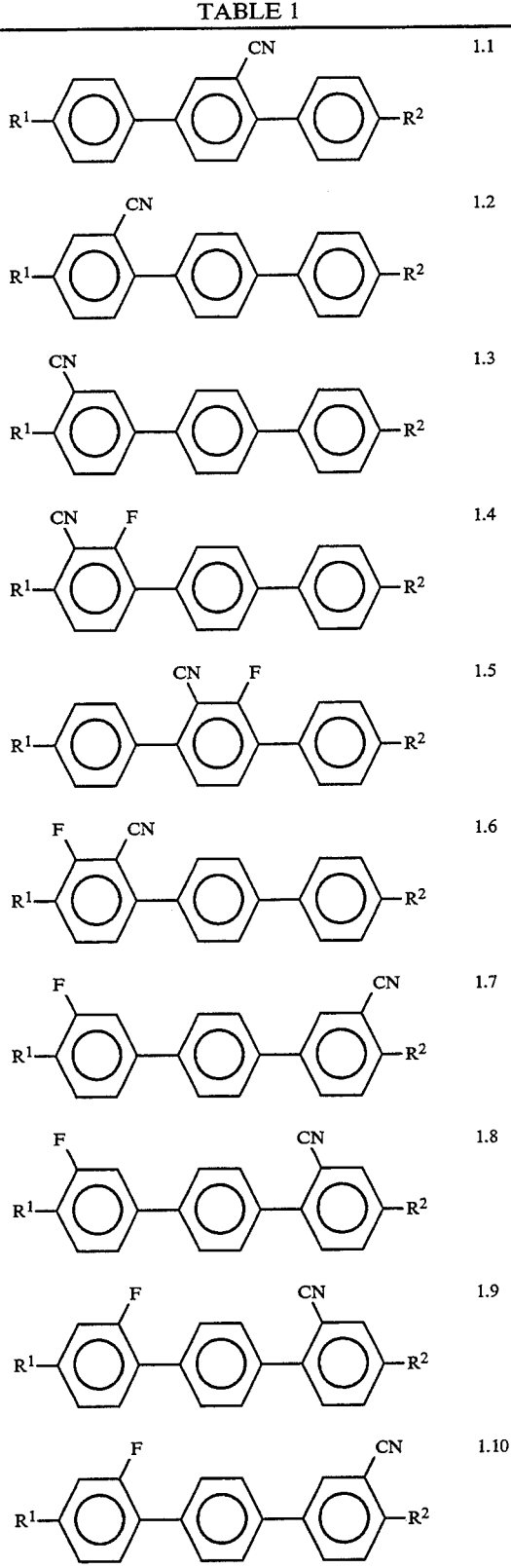

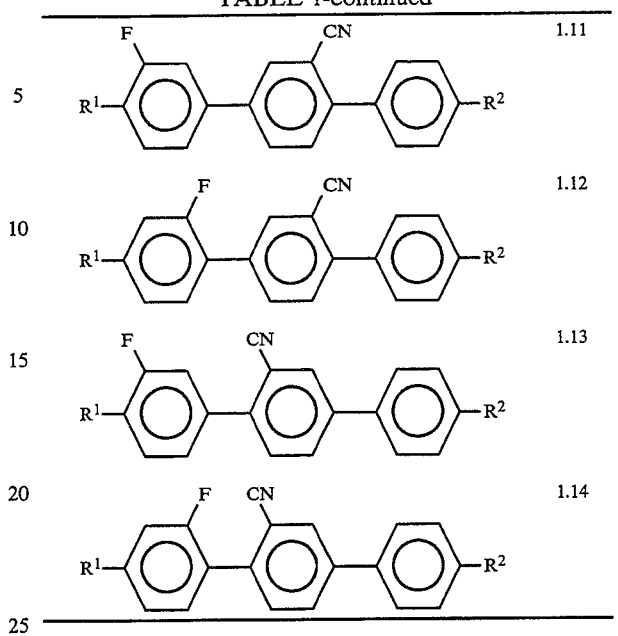

$R^1$, $R^2$=alkyl, alkoxy or alkynyl of the structures listed in Table 1, structures 1.1, 1.3, 1.4, 1.5, 1.6 and 1.10 are particularly preferred, especially 1.1, 1.3, 1.4, 1.10.

In compounds of formula I, IA or as listed in Table 1, $R^1$ and $R^2$ are preferably independently n-alkyl, n-alkoxy or n-alkynyl containing 3–12 especially 3–10 carbon atoms, or branched or asymmetrically substituted alkyl, alkoxy or alkynyl, which may be in an optically active or racemic form, but especially n-alkyl or n-alkoxy. $R^1$ and $R^2$ may be the same or different.

In a compound of formula 1, $R^1$ and $R^2$ may therefore be independently dently selected from the following preferred groups listed in Table 2 below:

TABLE 2

| n-alkyl | n-alkoxy | n-alkynyl |
|---|---|---|
| $C_3H_7$ | $C_3H_7O$ | $C_2H_5C{\equiv}C$ |
| $C_4H_9$ | $C_4H_9O$ | $C_3H_7C{\equiv}C$ |
| $C_5H_{11}$ | $C_5H_{11}O$ | $C_4H_9C{\equiv}C$ |
| $C_6H_{13}$ | $C_6H_{13}O$ | $C_5H_{11}C{\equiv}C$ |
| $C_7H_{15}$ | $C_7H_{15}O$ | $C_6H_{13}C{\equiv}C$ |
| $C_8H_{17}$ | $C_8H_{17}O$ | $C_7H_{15}C{\equiv}C$ |
| $C_9H_{19}$ | $C_9H_{19}O$ | $C_8H_{17}C{\equiv}C$ |
| $C_{10}H_{21}$ | $C_{10}H_{21}$ | $C_9H_{19}C{\equiv}C$ |
| $C_{11}H_{23}$ | $C_{11}H_{12}O$ | $C_{10}H_{21}C{\equiv}C$ |
| $C_{12}H_{25}$ | $C_{12}H_{25}O$ | |

Preferred asymmetrically substituted alkyl and alkoxy groups are 2-methylbutyl, 2-methylbutyloxy, 3-methylpentyl, 3-methylpentyloxy, 4-methylhexyl, 4-methylpentyl, 1-methylheptyl and 1-methylheptyloxy.

Preferred asymmetrically substituted alkynyl groups are:

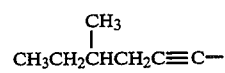

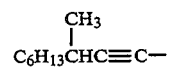

Compounds of formula I may be prepared via a number of synthetic routes, for example routes A - F shown in the accompanying FIGS. 1-11, route B providing some useful intermediates. The respective structural types which may be prepared using these routes are as follows, referring to Table 1 above:

| Structure | Route |
|---|---|
| 1.1 | A1, A2 |
| 1.2 | C1 |
| 1.3 | C1, C2 |
| 1.4 | D1, D2 |
| 1.5 | D3 |
| 1.6 | D4 |
| 1.7 | E1, E2 |
| 1.8 | E1 |
| 1.9 | E1 |
| 1.10 | E1, E2 |
| 1.11 | F1 |
| 1.12 | F2 |
| 1.13 | F3 |
| 1.14 | F4 |

Modifications to routes A-F to prepare compounds in which the substituents $R_1$ and $R_2$ of Table 1 are different to those illustrated in FIGS. 1 to 11 will be apparent to those skilled in the art of organic synthesis, for example the replacement of the alkyl or alkoxy groups R, $R^1$, $R^2$ R" by their perfluorinated analogues or by alkynyl or alkynyloxy groups.

Although the overall routes A-F and their end products are novel the individual steps use known reactions.

For example the following steps use the known coupling reaction between the halo-phenyl ring and the phenylboronic acid in the presence of tetra-(triphenyl-phosphine)-palladium (0): A11, A23, A24, C14, C23, C25, D13, D22, D42, D44, E12, E22, E23, F11, F21, F31, F32, F43, F The phenylboronic acids used in these steps may in turn be produced from the halophenyl precursor by the known method which first prepares a Grignard Reagent using Magnesium in tetrahydrofuron (THF) followed by a reaction with tri-isopropylborate then hydrolysis with hydrochloric acid. This procedure is used in steps B13, B22, C13, D41, D43, E11, F42.

In routes D1, D2, D3 and D4 the lateral $CO_2H$ group is introduced into the fluorinated ring using n-Butyl-lithium in hexane followed by reaction with carbon dioxide then hydrolysis. The $CO_2H$ group is then converted into the corresponding amide using oxalyl chloride and ammonia, followed by dehydration using thionyl chloride.

Other known reactions used in these routes are as follows:

A21, F45 - N-bromosuccinimide/dichloromethane 0° C.
A22, F46 - (i) $NaNO_2HCl$ (ii) KI
B11 - Friedel Crafts reaction, $RCOCl/AlCl_3$
B12, F48 - via hydrazine hydrate (F48a=direct use)
B21, C11, D21, F41 - $RBr/acetone/K_2CO_3$
C12 - $Br_2$
C21, P47 - R-C≡CH, $ZnCl_2$: $Pd(PPh_3)_4$
C22 - $H_2$, Pd/C Apart from standard reagents the starting materials for routes A-F are known or commercially available, eg from BDH Ltd or Fluorochem. A method for the preparation of the terphenyl starting point of route D3 is found in EP-A-0132377. In routes A-F when the starting compound may be made by one or more of the other routes this is indicated, eg (C13) in route C2 shows that this starting compound may be made via step C13.

It should also be noted that the products of steps D13, D22 and D43, and the starting compound for step D31 are protected by the claims of the Applicant's EP-0132377-B and U.S. Pat. No. 4,594,465.

To prepare compounds in which $R^1$ and/or $R^2$ contain fluorine, the appropriate perfluoroalkyl compounds may be used as starting points, eg in steps B11 or B22 etc.

Compounds in which $R^1$ and/or $R^2$ contain a COO or OOC group, e.g. RCOO- where R is alkyl may for example be prepared by removing a terminal $R^1$ or $R^2$ group which is alkoxy from a terphenyl product of formula I or IA using the known method of reaction with $BBr_3$ followed by hydrolysis to leave a terminal -OH group, followed by esterification of phenol with a carboxylic acid RCOOH or an acyl chloride RCOCl.

The C≡C group in compounds in which $R^1$ and/or $R^2$ is alkynyl is a reactive functional group and may for example be hydrated, eg using $HgSO_4/H_2SO_4$ or $B_3$ to yield terminally ketone substituted terphenyls, eg having terminal $—CO.CH_2$, —R or $—CH_2CO.$—R groups. Such ketones may be reduced to form the corresponding alcohols, i.e. $—CH(OH)CH_2$—R or $—CH_2CH(OH)$—R which themselves be esterified with a carboxylic acid to form the corresponding esters.

Alterately the ketones may be converted into cyanohydrins by reaction with HCN, leaving terminal groups of structure —C·N·OH—$CH_2$—R and —$CH_2$—C·CN·R. Such cyanohydrins may then be esterified eg with a carboxylic acid R"—COOH where R" is alkyl to yield terphenyls with one or more terminal substituent groups of structure:

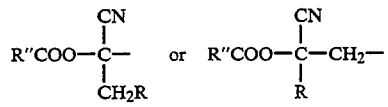

Also reaction of the C≡C group with halogens or hydrogen halides can lead to terphenyls of formula. I with halogenated terminal substituents $R^1$ and/or $R^2$. For example well known reactions of an alkyne substituent R-C≡C such as in the product of step C25 can lead in this way to R—$CX_2CX_2$—, R—CHX=CHX—, R—$CH_2CX_2$—) and R—$CX_2CH_2$— where X is a halogen eg chlorine.

Many terphenyls of formula I show liquid crystal phases, and also a high negative dielectric anisotropy ΔE. These are therefore useful components of liquid crystal materials, and therefore according to a further aspect of this invention there is provided a liquid crystal material, being a mixture of compounds, at least one being a terphenyl of formula I, preferably formula IA.

Such a liquid crystal material may be a nematic or smectic liquid crystal material.

A nematic liquid crystal material may therefore be a mixture of compounds at least one of which is a terphenyl of formula I, preferably one which exhibits a nematic liquid crystal phase. As terphenyls of formula I have a high negative ΔE they may usefully be mixed with other compounds which show nematic liquid crystal phases and which for example have a low ΔE, or a positive ΔE to provide a mixture of intermediate ΔE. As is well known in the liquid crystal art, the sign of ΔE (ie +ve or −ve) of a nematic liquid crystal material is chosen according to the kind of electro-optical device in which the material is to be used. Hence the availability of the high negative ΔE compounds of the invention is very advantageous. In particular the terphenyls of the invention are likely to be useful in liquid crystal mixtures which use the ECB effect.

The general classes of other compounds which may be included in a nematic liquid crystal material according to this aspect of the invention will be well known to those skilled in the liquid crystal art. Some examples of compounds having a low ΔE are listed below:

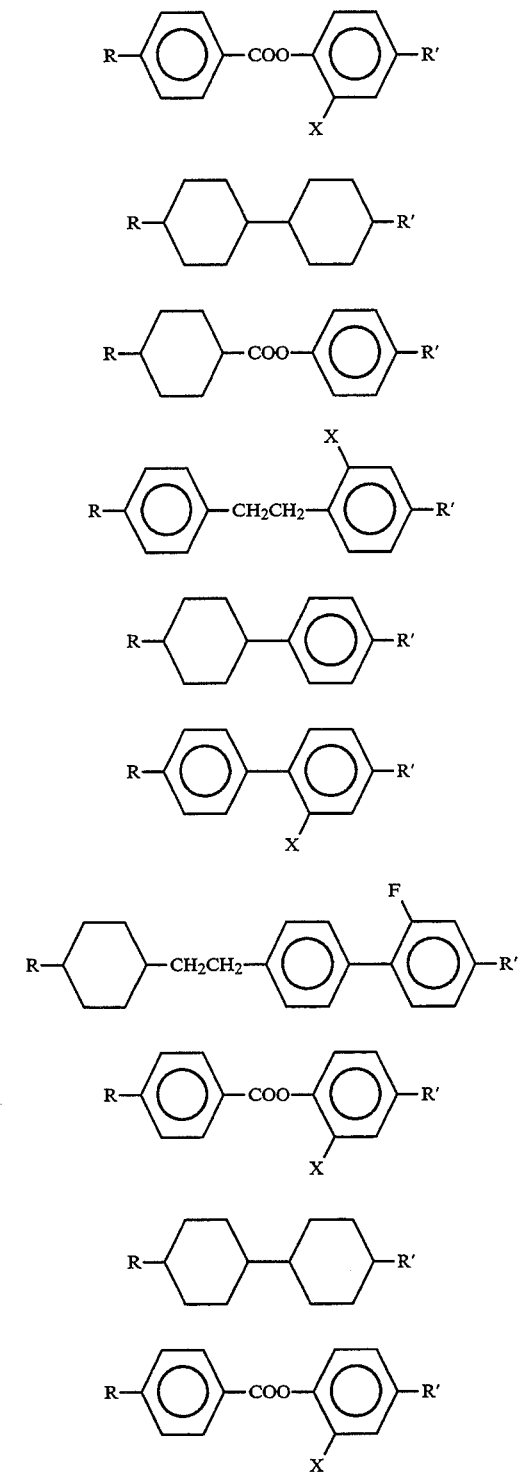

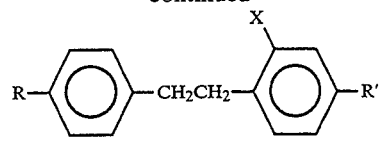

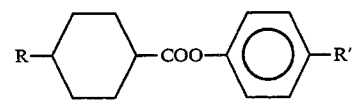

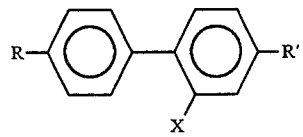

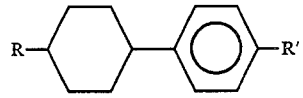

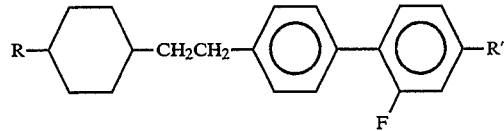

Some examples of compounds having a positive ΔE are listed below:

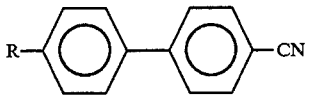

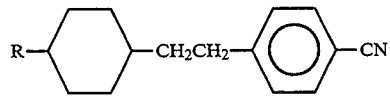

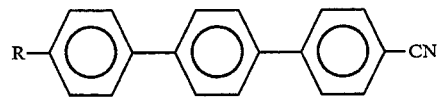

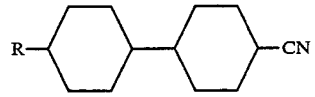

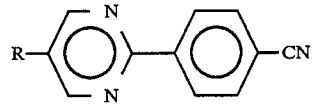

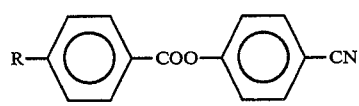

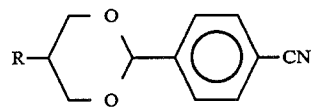

Where R and R' independently represent $C_1$–$C_8$ alkyl or alkoxy, and X represents F or H.

The nematic liquid crystal mixture of this aspect of the invention my also contain pleochrotc dyes, such as those described in EP-A-82300891, and/or One or more optically active compounds to induce the appearance of a cholesteric phase.

Typically but not exclusively a nematic liquid crystal mixture of this aspect of the invention contains:

Compounds of formula I: 5–95 wt %
Low $\Delta E$ compounds: 0–95 wt %
High +ve $\Delta E$ compounds: 9–95 wt %
Optically active compounds: 0–5 wt %
Pleochroic dyes: 0–5 wt %

The over-all sum of weight percentages being 100 wt %.

The invention also provides a smectic liquid crystal material which is a mixture of two or more compounds, at least one of which is a terphenyl of formula I, preferably of formula 1A, and especially of formula 1.1 or 1.4 of Table 1. This mixture preferably also contains in addition one or more other compounds which together- or separately show a smectic phase. The smectic phase is preferably $S_C$, $S_F$ or $S_I$/

Preferably the mixture of this aspect of the invention contains one or more terphenyls of formula I and one or more FTP's of formula II

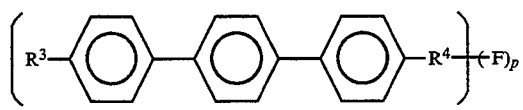

Formula II where $R^3$ and $R^4$ are independently selected from hydrogen, alkyl and alkoxy each containing 1–12 carbon atoms, p may be 1 or 2 and the fluorosubstituents(s) may occupy any of the available lateral substitution positions. Preferred FTP's for this aspect of the invention have a formula IIA, IIB or IIC.

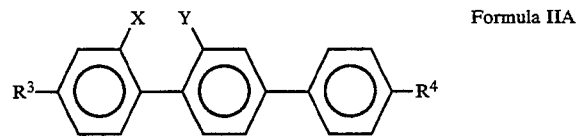

Formula IIA

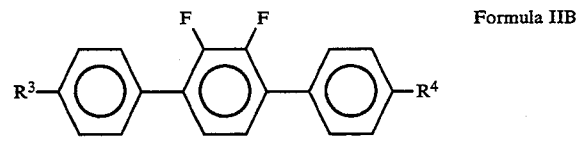

Formula IIB

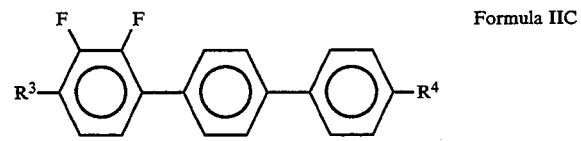

Formula IIC where $R^3$ and $R^4$ are as defined above, and where X and Y are independently selected from hydrogen and fluorine, at least one of X and Y being fluorine. Preferably $R^3$ and $R^4$ are n-alkyl or n-alkoxy containing 3–12 carbon atoms, especially 3–10.

$R^3$ and $R^4$ may be the same or different. Preferred n-alkyl and n-alkoxy groups from which $R^3$ and $R^4$ may be selected are those from which $R^1$ and $R^2$ are selected, as listed above, although the combinations of $R^1$ and $R^2$ need not be the same as $R^3$ and $R^4$ in the mixture.

Preferably X in formula IIA is hydrogen and Y is fluorine. The preparation of such FTPs is described for example in EP-A-0132377. The preparation of FTPs in which p is 2, eg of formula IIB and IIC is described in GB-A-8806220 filed 16-03-88, the contents of which are incorporated herein by reference.

The smectic liquid crystal material of this aspect of the invention may for example show an Sc phase at room temperature, and may be a mixture of one or more FTPs of formula IIA plus one or more terphenyls of the invention, or may be a mixture of one or more FTP's of formula IIB and or one or more FTP's of formula IIC plus one or more terphenyls of the invention.

The addition of one or more compounds of formula I to one or more FTPs of formula II often results in suppression of undesirable $S_B$ phases shown by the FTP, and may also result in a mixture showing an $S_C$ phase over a broader temperature range than the FTP. This is particularly so with FTP's of formula IIA. These effects may be manifested at quite low ratios of formula I compound(s) to FTP's, for example typically in the range 1:20 to 1:5 by weight % of formula I compound(s) to FTP(s).

Other compounds which show an $S_C$ phase and which may be used in mixtures of this aspect of the invention are the known compounds:

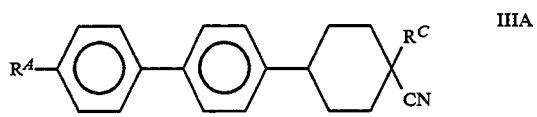

IIIA

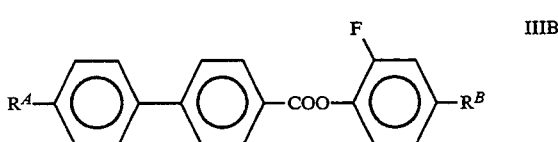

IIIB

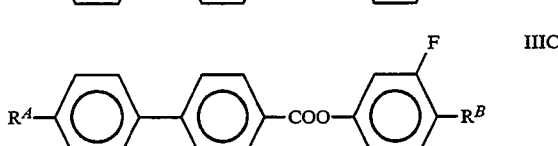

IIIC

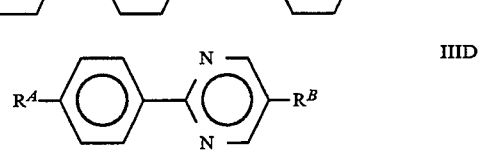

IIID where $R^A$, $R^B$ and $R^C$ independently contain 1–12 carbon atoms, $R^A$, and $A^B$ are independently n-alkyl or n-alkoxy, and $R^C$ is independently n-alkyl.

With the smectic mixtures of this aspect of the invention may be mixed one or more optically active compounds which induce the mixture to show an $S_C*$ phase and/or increase the $P_S$ of the mixture. The mixtures produced in this way are ferroelectric mixtures showing a $P_S$ value and are a further aspect of this invention. The use of terphenyls of the invention in such mixtures may result in advantageous $P_S$ values and switching times.

Many optically active compounds are known which may be used in this way. Preferred optically active compounds are those described in PCT GB 85/0512, eg

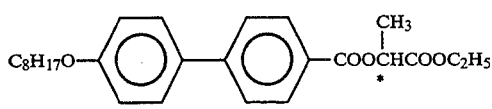

the compounds described in EP-A-0110299, eg

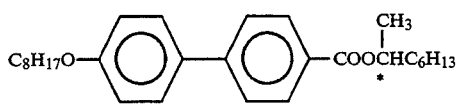

the compounds described in PCT/GB 87/00280, eg

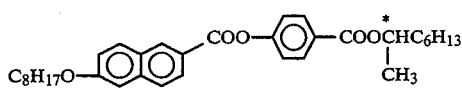

and in particular the compounds described in PCT/GB87/00441 which contain a COOCH(CN)R group where R is alkyl, for example:

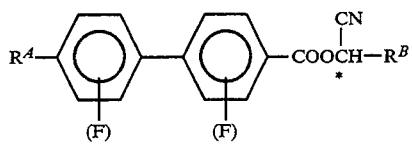

where $R^A$ is n-alkyl or n-alkoxy containing 5–12 carbon atoms, (F) indicates that the phenyl ring may carry a fluoro substituent, and $R^B$ is $C_1$-4 n-alkyl, cycloalkyl or a branched alkyl of formula:

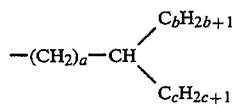

where a may be 0 or an integer 1–5, and each of b and c is an integer 1–6, preferably a being 0 and at least one of b or c being 1.

Preferred groups $R^B$ in compounds VII are methyl, —CH(CH$_3$)$_2$, —CH·C$_3$·CH$_2$CH$_3$ and cyclohexyl.

Additives if used in such mixtures may fulfill a number of functions. For example additional optically active compounds may be included to control the pitch of the $S_C{}^*$, phase such as the optically active amide compounds described in PCT GB 87/00223, eg

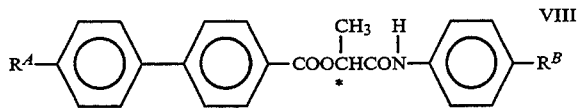

or the optically active terphenyls described in GB 8703103 eg

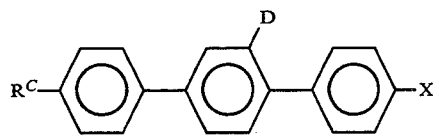

where $R^A$, $R^B$ and $R^C$, are independently n-alkyl or n-alkoxy containing 1–12 carbon atoms, D is F or C;, X is OOCCH(CH$_3$)OR", OCH(CH$_3$)COOR" or COOCH(CH$_3$)R" where R" is n-alkyl containing from 1 to 12 carbon atoms.

Additives may also serve the function of encouraging the formation of an $S_A$ phase at a temperature above that of the $S_C{}^*$ to assist in alignment of the mixture with the electrodes of an electro-optic device.

Additives may also suppress undesirable phases such as $S_A$ or $S_B$ so that these occur at temperatures far away from the working temperature range, eg

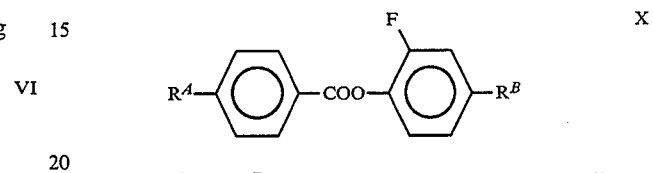

where $R^A$ and $R^B$ are independently n-alkyl or n-alkoxy containing 1–12 carbon atoms.

Typically but not exclusively a smectic C liquid crystal material of this aspect of the invention is a mixture having a composition as follows:

| | |
|---|---|
| One or more compounds which show together or separately a room temperature $S_C$ phase, especially of formulae IIA, IIB IIC or IIIA. | 50–95 wt % |
| Compound(s) of formula I. | 5–50 wt % |
| | preferably 5–25 wt % |
| Optically active compound(s), at least some being present if the mixture is to show an $S_C$ phase. | 0–25 wt % |
| Additive(s) | 0–20 wt % |
| Total | 100 wt % |

The nematic and ferroelectric smectic liquid crystal mixtures of the invention may be used in any of the known types of liquid crystal electro-optical display device which use such materials, for example as described in the two Appl. Phys. Left. references mentioned above.

The construction and method of operation of such liquid crystal electro-optical devices is well known. Generally such a device comprises two substantially parallel substrates, at least one of which is optically transparent, and having electrodes on their facing surfaces, and sandwiched between them a liquid crystal material. The application of a voltage across the liquid crystal material via the electrodes causes a change in the optical properties of the liquid crystal material to produce a visible effect. Suitable dimensions, voltages and other parameters for such a device will be apparent to those skilled in the art.

Figure 12:
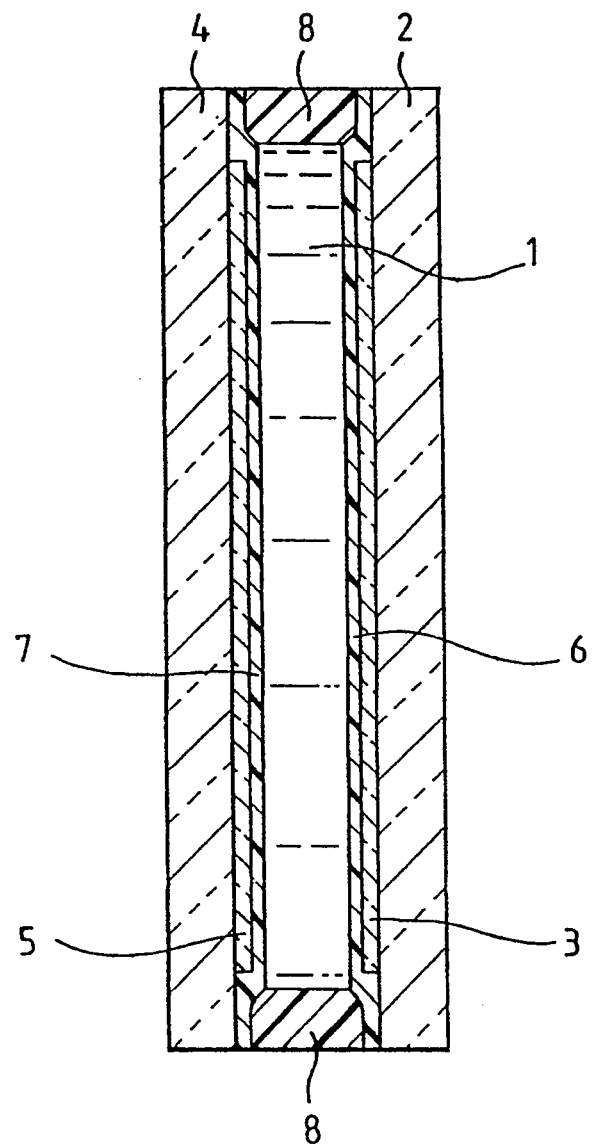
FIG. 12 is a cross-sectional view of a liquid crystal electro optical display device containing a liquid crystal material of the invention.

The invention will now be described by way of example only with reference to the accompanying FIGS. 1–11 whch show preparative routes for terphenyls of the invention and FIG. 12 which shows a cross section through a liquid crystal device.

In the following examples all temperatures are in °C. The abbreviation N=nematic, $S_A$=smectic A, $S_C$ =smectic C, $S_?$ and $S_{??}$unidentified smectic phase I=isotropic liquid K=solid crystal. Liquid crystal transitions shogun ( ) are virtual transitions seen on supercooling.

PREPARATION EXAMPLES
EXAMPLE 1

Using routes A1, A2, B1 and B2 the following compounds of structure 1.1 were made:

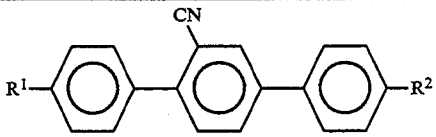

| $R^1$ | $R^2$ | Liquid crystal transition temps (°C.) |
|---|---|---|
| n-$C_5H_{11}$ | n-$OC_6H_{13}$ | K 35.5 $S_A$ 97.5 I |
| n-$C_5H_{11}$ | n-$OC_8H_{17}$ | K 33.5 $S_A$ 103.0 I |
| n-$C_6H_{13}O$ | n-$C_5H_{11}$ | K 48.5 ($S_C$ 29.5) N 77.5 I |
| n-$C_8H_{17}O$ | n-$C_5H_{11}$ | K 35 0 $S_C$ 42.0 N 78.0 I |
| n-$C_6H_{13}O$ | n-$OC_6H_{13}$ | K 101.5 ($S_C$ 61.0) $S_A$ 110.0 N 114.0 I |
| n-$C_5H_{11}$ | n-$C_5H_{11}$ | $S_A$ -N (33.5) N-I (38.0) K-I 40.0 |
| n-$C_6H_{13}$ | n-$OC_6H_{13}$ | |

Route B1
Step B11
The compound

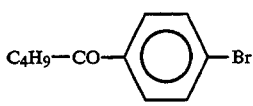

was prepared by a Friedel - Crafts reaction between bromobenzene and n-pentanoyl chloride ($C_4H_9COCl$) in the presence of aluminium chloride.

Step B12

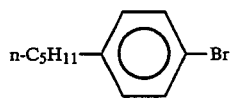

A mixture of the product of step B11 (77.1 g, 0.32 mol), hydrazine hydrate (46.4 g, 0.93 mol) and potassium hydroxide (59.0 g, 1.05 mol) in diethylene glycol (250 ml) was heated at 130° C. for 2 h. The excess of hydrazine hydrate was distilled off and the temperature was raised to 0° C. for 2 h. The cooled mixture was poured into 18% hydrochloric acid, the product was extracted into ether (twice), and the combined ethereal extracts were washed with water and dried ($MgSO_4$). The solvent was removed in vacuo and the residue was distilled to yield a colourless liquid. The identity of the product was confirmed by nmr, ir and MS. Yield 58,1 g (80%), bp 145°-148° C. at 20 mm Hg.

Step B13

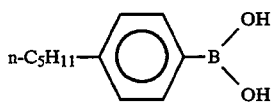

A solution of the Grignard reagent prepared from the product of step B12 (24.0 g, 0.11 mol) and magnesium (2.95 g, 0.12 mol) in dry THF (85 ml) was added dropwise to a stirred, cooled (−78° C.) solution of tri-isopropyl borate (39.8 g, 0.21 mol) in dry THF (25 ml) under dry nitrogen. The stirred mixture was allowed to warm to room temperature overnight and stirred for 1h with 10% hydrochloric acid (120 ml) at room temperature. The product was extracted into ether (twice), and the combined ethereal extracts were washed with water and dried ($MgSO_4$). The solvent was removed in vacuo to afford a soft off-white solid. Yield 19.3 g (95%). The identity of the product was confirmed as above.

Route B2
Step B21

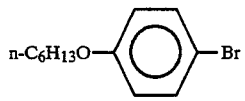

A solution of 1-bromohexane (60.0 g, 0.36 mol.) in acetone (150 ml) was added dropwise to a stirred mixture of 4-bromophenol (71.0 g, 0.41 mol) and potassium carbonate (120.0 g, 0.87 mol) in acetone (600 ml) at room temperature. The stirred mixture was heated under reflux (90°-95° C.) for 43 h (ie until glc analysis revealed an absence of 1-bromohexane). The product was extracted into ether (twice), and the combined ethereal extracts were wasted with water, 5% sodium hydroxide, water and dried ($MgSO_4$). The solvent was removed in vacuo and the residue was distilled to yield a colourless liquid. Yield 79.4 g (86%), bp 100°-110° C. at 0.1 mm Hg. The identity of the product was confirmed as above.

Step B22

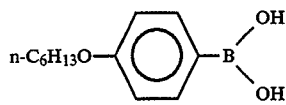

A solution of the Grignard reagent, prepared from the product of step B21 (72.0 g, 0.28 mol) and magnesium (7.75 g, 0.32 mol) in dry THF (220 ml) was added dropwise to a stirred, cooled (−78° C.) solution of tri-isopropyl borate (109.1 g, 0.58 mol) in dry THF (40 ml) under dry nitrogen. The stirred mixture was allowed to warm to room temperature overnight and stirred for 1 h with 10% hydrocholoric acid (320 ml) at room temperature. The product was extracted into ether (twice), and the combined ethereal extracts were washed with water and dried ($MgSO_4$). The solvent was removed in vacuo to afford a colourless solid. Yield 61.2 g (99%) mp 80°-85° C. The identity of the product was confirmed as above.

Route A1
Step A11

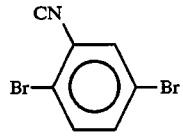

Bromine (44.0 g, 0.275 mol) was added dropwise to a mixture of benzonitrile (10.0 g, 0.097 mol) and aluminum chloride (42.0 g, 0.31 mol) at room temperature. The mixture was heated at 70° C. for 3.5 h and poured into ice/water. The product was extracted into ether (twice) and the combined ethereal extracts were washed with sodium thiosulphate and dried (MgSO₄). The solvent was removed in vacuo to afford an off-white solid (23.4 g) (glc analysis revealed presence of three components) which was recrystallised from benzene to give colourless crystals. Yield 3.1 g (12%). mp 144°–45° C. (lit 144°–145° C.). The identity of the product was confirmed as above.

Note: The low yield was probably due to insufficient reaction time or too low a temperature being used as glc analysis of the crude product revealed the presence of starting material and what is suspected to be 3-bromobenzonitrile.

Step A12

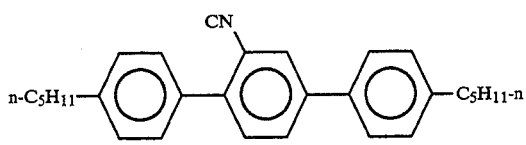

A solution of 4-pentylphenylboronic acid (B1D) (2.88 g, 0.015 mol) in ethanol (50 ml) was added dropwise to a stirred mixture of 2,5-dibromobenzonitrile (1.40 g, 5.36 mol) and tetrakis-(triphenylphosphine) palladium (0) (0.3749 g, 0.325 mmol) in benzene (30 mi) and 2M-sodium carbonate (30 ml) at room temperature under dry nitrogen. The stirred mixture was heated under reflux (90°–95° C.) for 18 h (ie until glc analysis revealed absence of starting material), cooled and stirred for 1 hr at room temperature with 30% hydrogen peroxide (5 ml). The mixture was filtered, the filtrate was washed with ether (twice), and the combined ethereal phases were washed with water and dried (MgSO₄). The solvent was removed in vacuo and the residue was purified by column chromatography [silica gel/petroleum fraction (bp 40°–60° C) - dichloromethane, 2:1] to give a colourless solid which was recrystallised from ethanol to yield fine colourless crystals. Yield 1.13 g (53%). The identity of the product was confirmed as above. The product showed the following liquid crystal transitions (°C.): K-I 40.0, S₄-N (33.5), N-I (38.0)

Step A12

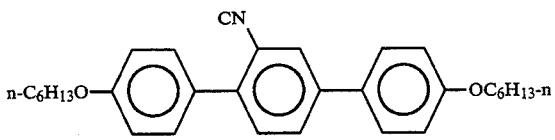

A solution of 4-hexoxyphenylboronic acid (B22) (3.33 g, 0.015 mol) in ethanol (70 ml) was added dropwise to a stirred mixture of 2,5-dibromobenzonitrile (1.30 g, 4.98 mmol) and tetrakis-(triphenylphosphine) palladium (0) (0.3554 g, 0.308 mmol) in benzene (30 ml) and 2M-sodium carbonate (30 ml) at room temperature under dry nitrogen. The stirred mixture was heated under reflux (90°–5° C.) for 21 h until glc analysis revealed absence of starting material), cooled and stirred for 1 hr at room temperature with 30% hydrogen peroxide (5 ml). The mixture was filtered, the filtrate was washed with ether (twice), and the combined ethereal phases were washed with water and dried (MgSO₄). The solvent was removed in vacuo and the residue was purified by column chromatography [silica gel/petroleum fraction (bp 40°–60° C.)-dichloromethane, 2:1] to give a colourless solid which was recrystallised from ethanol t6 give colourless crystals. Yield 0.87 g (38%).

Route A²

The 4-alkyl-and 4-alkoxy-phenylboronic acids prepared using route B exemplified above were used to prepare compounds of formula 1.1 via route A 2.

Step A21

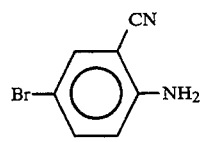

N-Bromosuccinimide (NBS) (37.71 g, 0.21 mol) was added in small portions over 40 mins to a stirred, cooled (−10°–0° C.) solution of 2-aminobenzonitrile (25.00 g, 0.21 mol) in dry dichloromethane (150 ml) under dry nitrogen. The mixture was stirred at 0° C. for 1 h 10 mins (glc analysis revealed a complete reaction) and washed with a large amount of water. The aqueous layer was washed with dichloromethane and the combined organic phases were washed with water and dried (MgSO₄). The solvent was removed in vacuo to give a red/purple solid (39 g, 94%) mp=92°–94° C.

Step A22

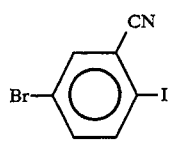

A stirred mixture of 2-amino-5-bromobenzonitrile (25.00 g 0.13 mmol) and 36% (conc) HCl (110 ml) was gently warmed to obtain a solution, then cooled to −5° C. and a solution of sodium nitrite (10.50 g, 0.15 mol) in water (50 ml) was added dropwise whilst maintaining the temperature at −5° C. The mixture was stirred at 0° C. for ½hr. cyclohexane was added, a solution of potassium iodide (43.5 g, 0.26 mol) was added dropwise at between 5 and 10° C. The mixture was stirred at room temperature for a few hours (or overnight for convenience), then warmed gently for 10 mins to ensure complete reaction. The product was extracted into ether (twice), the combined ethereal phases were washed successively with sodium metabisulphite, 10% sodium hydroxide, water and dried (Mg SO₄). The solvent was removed in vacuo to give a sand-coloured solid (35 g, 87%). mp =113°–114° C Step A23

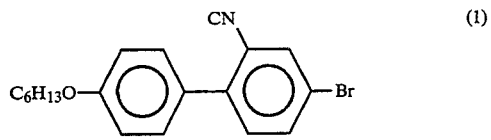

(1)

A solution of 4-hexoxyphenylboronic acid ( see step B22) ( 1.56 g, 7.03 mmol) in ethanol (minimum amount possible (20 ml) was added dropwise to a stirred mixture of 5-bromo-2-iodobenzonitrile (1.80 g, 5.84 mmol) and tetrakis (triphenylphosphine) palladium (0) (abbreviated hereinafter to TTP) (0.35 72 g, 0.31 mmol) in benzene (30 ml) and 2M-sodium carbonate (30 ml). The stirred mixture was heated under reflux (95° C.) for 1¼ hr (ie until glc analysis revealed a satisfactory starting material—product ratio (1:10)). The product was extracted into ether (twice), the combined ethereal extracts were washed with brine and dried (MgSO₄). The solvent was removed in vacuo and the residue was purified by column chromatography (silica gel/petroleum fraction (bp 40°–60° C.)—dichloromethane, 1:1) to give a colourless solid (1.72 g, 82%).

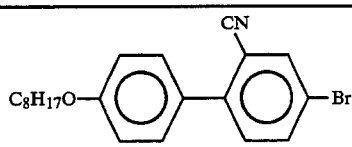
(2)

| 5-bromo-2-iodobenzonitrile | 2.50 g, 8.12 mmol |
| 4-octoxyphenylboronic acid (via route B2) | 2.44 g, 9.76 mmol |
| TTP | 0.4927 g 0.43 mmol |

The method was the same as that above. The mixture was reheated under reflux (95° C.) for 2 h. Purified by column chromatography [silica gel/petroleum fraction (bp 48°–60° C.)-dichloromethane, 1:1] to give a colourless solid (2.50 g, 80%).

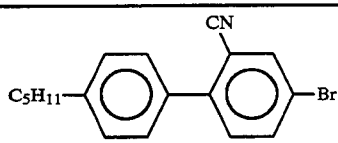
(3)

| 5-bromo-2-iodobenzonitrile | 3.50 g, 0.001 mol |
| 4-pentylphenylboronic acid (route B1) | 2.53 g, 0.013 mol |
| TTP | 0.6421 g, 0.56 mmol |

The method was the same as that above. The mixture was heated under reflux (295° C.) for 2 h. Purified by column chromatography (silica gel/petroleum fraction (bp 40°–60° C.), dichloromethane, 1:1) and distillation (Kugel rohr, 0.1 mm Hg) to give a give yellow liquid (2.67 g, %).

Step A24

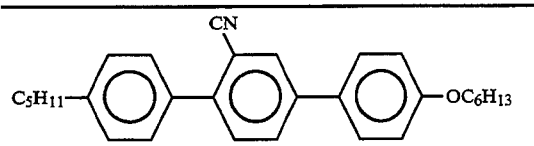
(1)

| 4-bromo-2-cyano-4¹-pentylbiphenyl (A23(3)) | 0.34 g, 1.0 mmol |
| 4-hexoxyphenylboronic acid (B22) | 0.44 g, 1.98 mmol |
| TTP | 0.1645 g, 0.14 mmol |

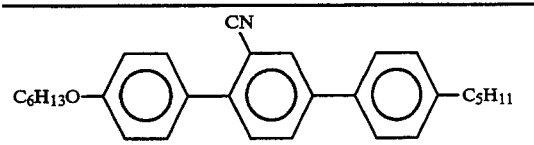
(2)

| 4-bromo-2-cyano-4¹-hexoxybiphenyl (A23(1)) | 1.50 g, 4.19 mmol |
| 4-pentylphenylboronic acid (B13) | 1.05 g, 5.47 mmol |
| TTP | 0.314 g, 0.27 mmol |

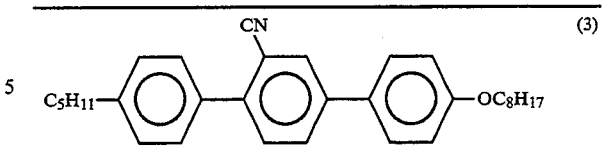
(3)

| 4-bromo-2-cyano-4¹-pentylbiphenyl (A23(3)) | 1.30 g, 3.96 mmol |
| 4-octoxypenylboronic acid (via route B22) | 1.19 g, 4.76 mmol |
| TTP | 0.265 g, 0.23 mmol |

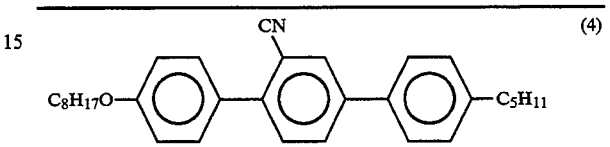
(4)

| 4-bromo-2-cyano-4¹-octoxybiphenyl (from A23(2)) | 1.48 g, 3.83 mmol |
| 4-pentylphenylboronic acid (from B13) | 1.01 g, 5.26 mmol |
| TTP | 0.2812 g, 0.34 mmol |

In each case the method used was treat of step A23 above. The mixture in case (2) was heated under reflux for 17 hours, in cases (1) and (3) for 21 hours, and case (4) for 22 hours, i.e. until analysis revealed a complete reaction. The product is purified by column chromatography (silica gel/petroleum formation (bp 40–60)-dichloromethane 1:1) to afford solids which were recrystallised from ethanol. The product of (2) was pale yellow and so was decolourised with charcoal.

Yield:
(1) colourless crystals (0.26%, 61%)
(2) colourless plates (0.80 g, 44%)
(3) colourless crystals (1.18 g, 66%)
(4) colourless solid (1.16 g, 67%)

EXAMPLE 2

Using route C1 the following compounds of structure 1.3 were prepared:

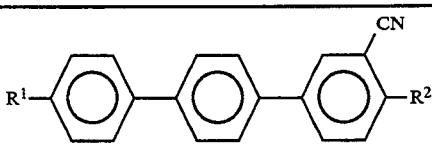

| $R_1$ | $R_2$ | Liquid Crystal Transition Temp |
|---|---|---|
| n-C₅H₁₁ | OC₈H₁₇-n | K 62.0 SA 160 I |
| n-C₅H₁₁ | OC₆H₁₃-n | K 62.0 SA 163.5 I |

Step C11

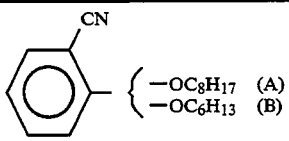
(A) —OC₈H₁₇
(B) —OC₆H₁₃

| 2-hydroxybenzonitrile | A 7.50 g, 0.063 mol |
| | B 8.10 g, 0.068 mol |
| 1-bromo-octane | A 14.00 g, 0.127 mol |
| 1-bromohexane | B 13.50 g, 0.082 mol |
| Potassium Carbonate | A 17.50 g 0.127 mol |

-continued

| | |
|---|---|
| B | 18.77 g 0.136 mol |

The experimental procedure was the same as for Step B21 described above. Yield: A 13.909 (96%) bp 130°–135° at 0.05 mm Hg; B 13.11 g (95%) bp 115°–518° at 0.1 mm Hg.

Step C12

[Structure: Br–C₆H₃(CN)–OC₈H₁₇ (A) / –OC₆H₁₃ (B)]

| Bromine | A 18.70 g, 0.117 mol |
| | B 19.32 g 0.12 mol |
| C11 product | A 13.50 g, 0.058 mol |
| | B 12.25 g, 0.060 mol |

The bromide was added dropwise during 15 minutes to a stirred solution of the C11 product in chloroform (30 ml) at room temperature. The stirred solution was refluxed for 42 hours (glc showed a complete reaction). The cooled solution was washed with sodium metabisulphite, water, then dried (Mg SO₄). The solvent was removed vacuo in give an off-white solid. Yield: A 17.50 g (97%) mp 36°–37°, B 16.10 g (95%) low melting around 15°.

Step C13

[Structure: $C_5H_{11}$–biphenyl–B(OH)₂]

| 4'-bromo-4-pentylbiphenyl | 9.35 g |
| magnesium | 0.871 g |
| tri-isopropyl borate | 11.66 g |

The experimental procedure was the same as for steps B13 and B22. The crude yield was 8.29 g, 100%.

Step C14

[Structure: $C_5H_{11}$–biphenyl–C₆H₃(CN)–OR]

| –OC₈H₁₇ (A) |
| –OC₆H₁₃ (B) |

| (A) | C12 product (A) | 1.55 g, 5.00 mmol |
| | C13 product | 1.75 g, 6.53 mmol |
| | TPP | 0.38 g, 0.33 mmol |
| (B) | C12 product (B) | 1.55 g, 5.50 mmol |
| | C13 product | 1.91 g, 7.13 mmol |
| | TTP | 0.39 g, 0.34 mmol |

The experimental procedure was the same as for Step A23 above. The crude product was purified by column chromatography (silica gel/petroleum fraction (bp 40°–60°) dichloromethane 2:1) to give a colourless solid which was recrystallised from ethanol-ethylacetate (2:1) to yield colourless crystals. Yield: A 1.85 g (82%), B 1.10 g (47%).

EXAMPLE 3

Using route E1 the compound of structure 1.10:

[Structure: n-$C_5H_{11}$–C₆H₃(F)–C₆H₄–C₆H₃(CN)–OC₈H₁₇-n]

was prepared. Liquid crystal transitions were K 48.0 $S_A$ 118.0 I.

Step E11

[Structure: n-$C_5H_{11}$–C₆H₃(F)–C₆H₄–B(OH)₂]

| 4'-bromo-2-fluro-4-pentylbiphenyl | 9.90 g |
| Magnesium | 0.871 g |
| Triisopropylborate | 11.66 g |

The experimental procedure was the same as for Step B13 above. Crude yield: 8.85 g, 100%.

Step E12

| 5-bromo-2-octoxybenzonitrile (C12A) | 1.30 g, 4–19 mmol |
| E11 product | 1.56 g, 5.45 mmol |
| TTP | 0.28 g, 0.24 mol |

The experimental procedure was the same as for step A23 above. The crude product was purified by column chromatography (silica gel/petroleum fraction (bp 40°–60°) dichloromethane 2:1) to give a colourless solid which was recrystallised from ethanol to give colourless crystals.

EXAMPLE 4

Using route D2 the following compounds of structure 1.4 was prepared:

[Structure: $R^1$–C₆H₃(CN)(F)–C₆H₄–C₆H₄–$R^2$]

| $R_1$ | $R_2$ | Liquid Crystal Transition Temps |
|---|---|---|
| n-$C_6H_{13}O$— | $nC_5H_{11}$ | K 100.5 $S_A$ 167.0 I |
| n-$C_8H_{17}O$— | $nC_5H_{11}$ | K 100.0 $S_A$ 163.5 I* |

*The extrapolated dielectric anistropy ΔE of the compound was measured to be −9.5.

Step D21

[Structure: Br–C₆H₃(F)– with –OC₈H₁₇ (A) / –OC₆H₁₃ (A)]

-continued

| (A) | 4-bromo-3-fluorophenol | 6.00 g |
| --- | --- | --- |
| | 1-bromo-octane | 7.30 g |
| | potassium carbonate | 10.00 g |
| (B) | 4-bromo-3-fluorophenol | 10.00 g |
| | 1-bromohexane | 10.37 g |
| | potassium carbonate | 14.50 g |

The experimental procedure was the same as for Step B21 above. Yields: A 9.01 g, 96% as a colourless liquid bp 140°–142° at 0.5 mm Hg; B 13.71 g, 96%.

Step D22

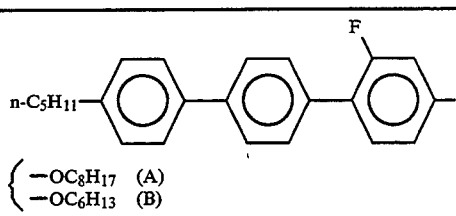

$\left(\begin{array}{ll} -OC_8H_{17} & (A) \\ -OC_6H_{13} & (B) \end{array}\right.$

| (A) | Step D21 product | 2.00 g, 6.60 mmol |
| --- | --- | --- |
| | Step C13 product | 2.30 g, 8.58 mmol |
| | TTP | 0.60 g, 0.52 mmol |
| (B) | Step D21 product | 1.50 g, 5.45 mmol |
| | Step C13 product | 1.90 g, 7.10 mmol |
| | TTP | 0.50 g 0.43 mmol |

The experimental procedure was the same as for Step A23 above. The crude products were purified by column chromatography (silica gel/petroleum fraction (bp 40°–60°) dichloromethane, 3:1) to yield colourless solids which were recrystallised from ethanol-ethyl acetate (2:1) to yield colourless crystals. Yield: A 2.30 g, 78%; B 1.46 g, 64%.

These products showed liquid crystal phases as below:

(A) K 69.0 ($S_K$ 25.0 $S_J$ 43.0) $S_C$ 119.0 N 158.0 I
(B) K 83.5 ($S_K$ 48.5 $S_J$ 62.0) $S_C$ 105.0 N 166.0 I

Step D23

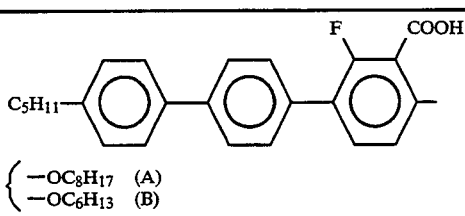

$\left(\begin{array}{ll} -OC_8H_{17} & (A) \\ -OC_6H_{13} & (B) \end{array}\right.$

| (A) | Step D22 product | 1.50 g, 3.36 mmol |
| --- | --- | --- |
| | n-butyl lithium | 0.50 ml 10.0M in hexane, 5.00 mmol |
| (B) | Step D22 product | 1.25 g, 2/99 mmol |
| | n-butyl lithium | 1.20 ml 2.5M in hexane, 3.00 mmol |

The solution of n-butyl lithium was added dropwise to the solution of the appropriate D22 product in dry THF (80 ml) under dry nitrogen with stirring, cooled to −78° C. In the case of (A) the mixture was maintained under these conditions for 6 hours, and for (B) for 5 hours. The mixture was then poured into a solid CO$_2$/ether slurry. 10% hydrochloric acid was added, the aqueous layer was washed with ether and the combined ethereal extracts were washed with water and dried (Mg SO$_4$). The solvent was removed in vacuo to give colourless solids. Yields: (A) 1.65 g, (B) 1.45 g (tic analysis revealed the presence of some starting materials).

Step D24

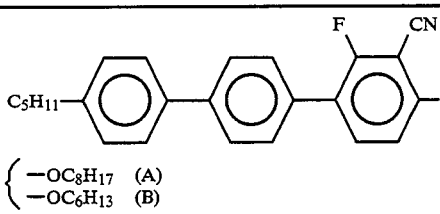

$\left(\begin{array}{ll} -OC_8H_{17} & (A) \\ -OC_6H_{13} & (B) \end{array}\right.$

| (A) | Step D23 product | 1.65 g 3.37 mmol |
| --- | --- | --- |
| | oxalyl chloride | 1.00 g 7.87 mmol |
| | 35% ammonia | 30 ml |
| | DMF | 8 drops |
| | thionyl chloride | 4.10 g, 0.034 mol |
| (B) | Step D23 product | 1.45 g 3.14 mmol |
| | oxalyl chloride | 0.80 g 6.30 mmol |
| | 35% ammonia | 25 ml |
| | DMF | 2 drops |
| | thionyl chloride | 3.70 g, 0.03 mol |

A solution of the oxalyl chloride in dry benzene (30 ml) was added dropwise to a stirred solution of the Step D23 product and DMF in dry benzene (30 ml) at room temperature. The mixture was stirred at room temperature overnight and the excess of oxalyl chloride and benzene were removed in vacuo. The residue was dissolved in diglyme (10 ml) and added dropwise to the gently stirred 35% ammonia. the resulting precipitate was filtered off and dried (Ca Cl$_2$) in vacuo (0.1 mm Hg) to give a colourless solid. A solution of the thionyl chloride in dry DMF (30 ml) was added dropwise to a stirred solution of this solid in dry DMF (30 ml). The mixture was stirred at room temperature overnight and poured onto ice/water. The product was extracted into ether (twice), the combined ethereal extracts were washed with water, sodium hydrogen carbonate, water and dried (MgSO$_4$). The solvent was removed in vacuo and the residue was purified by column chromatography [silica gel/petroleum fraction (bp 40°–60° C.)-dichloromethane, 2:1] to give a colourless solid. Inthe case of (A) this was recrystallised from ethyl acetate, and (B) from ethanol-ethyl acetate (2:1) to yield colourless crystals. Yield A: 0.21 g, 13% based on D22 product; B 0.20 g, 15% based on D22 product.

EXAMPLES OF LIQUID CRYSTAL MIXTURES

EXAMPLE 5

Properties of mixtures of two cyano-terphenyls of formula 1.1, ie (A) where both R and R are n-pentyl, and (B) where both R$^1$ and R$^2$ are n-hexyloxy, with an FTP of formula:

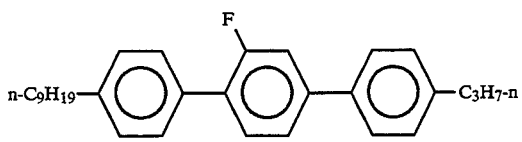

are listed below together with properties of the pure FTP.

EXAMPLE 5

| | Transitions (°C.) | | | | | |
|---|---|---|---|---|---|---|
| | K | $S_B$ | $S_C$ | $S_A$ | N | I |
| 100% FTP | . 46 | . (35) | . 52.2 | . 89 | . 126.5 | . |
| 95% FTP / 5% (A) | . 42.5 | . — | . 48 | . 80 | . 122 | . |
| 85% FTP / 15% (A) | . 36 | . — | . 39 | . 60.5 | . 113 | . |
| 94% FTP / 6% (B) | . 44 | . — | . 55.5 | . 82 | . 125 | . |
| 85% FTP / 15% (B) | . 44 | . — | . 56 | . 78 | . 123 | . |

From these results it is clear that the mixing of a cyanoterphenyl of the invention with an FTP suppresses the $S_B$ phase of the FTP, in some cases lowers the temperature at which the $S_C$ phase of the FTP appears on heating, and in others broadens the temperature range over which the $S_C$ phase persists.

In the following examples the following mixtures and compounds are referred to by the abbreviations indicated:

Mixture H1

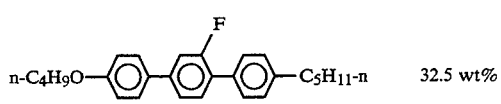 32.5 wt%

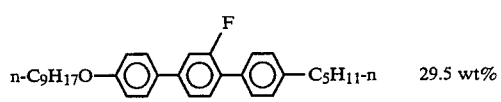 29.5 wt%

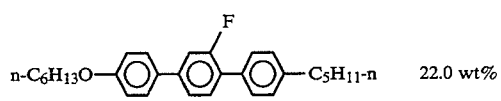 22.0 wt%

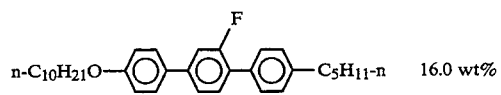 16.0 wt%

(ie a mixture of FTP's of formula IIA (Y=F) described above) This mixtures shows liquid crystal transition temperatures: K 31.8 S? 40.4 S??50.6 $S_C$ 107 N 160 I Mixture H2

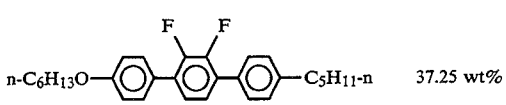 37.25 wt%

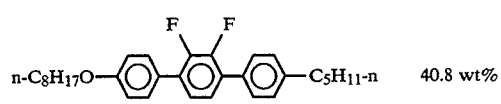 40.8 wt%

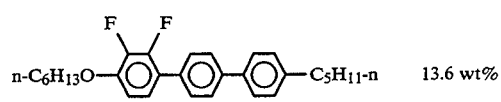 13.6 wt%

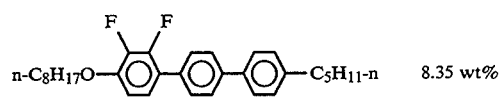 8.35 wt%

(ie a mixture of FIT's of formula IIB and IIC described above) This mixture shows liquid crystal transition temperatures: <20 Sc 96.9 N 146.2 I Mixture H3

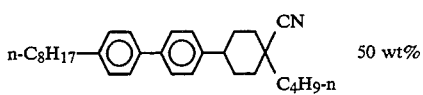 50 wt%

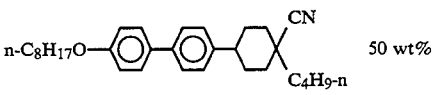 50 wt%

(ie a mixture of compounds of formula IIIA)
This mixture shows liquid crystal transition temperatures: S?41.5 Sc 87 $S_A$ 120.7 N 134.5 I Dopant 1.

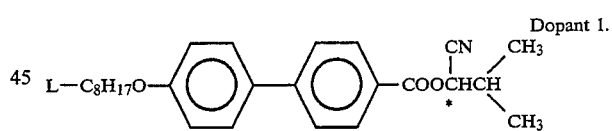

Dopant 2.

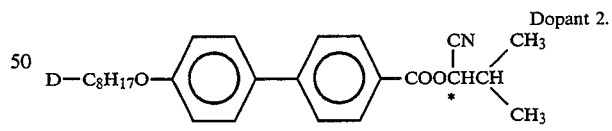

(ie formula VII described above)

EXAMPLE 6

Mixture H1 + 10%

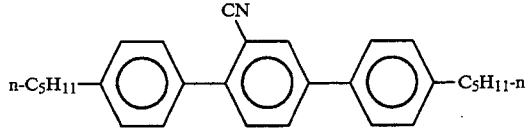

K 13 Sc 88.4 N 134.3 I

Addition of the cyanoterphenyl results in increased Sc range and elimination of low temperature undesirable smectic phases relative to pure H1.

EXAMPLE 7

Mixture H1 + 10% n-C$_6$H$_{13}$—⟨◯⟩—⟨◯⟩(CN)—⟨◯⟩—OC$_6$H$_{13}$-n

K 16.5 Sc 96.4 N 153 I

Increased Sc range, elimination of lower smectic phases.

EXAMPLE 8

Mixture H3 + 10% n-C$_5$H$_{11}$—⟨◯⟩—⟨◯⟩(CN)—⟨◯⟩—C$_5$H$_{11}$-n

< −20 Sc 66 SA 106.6 N 124 I

Supercooled to much lower temperature than pure H3, no lower smectic phases.

EXAMPLE 9

| | |
|---|---|
| Mixture H2 | 72 wt % |
| n-C$_8$H$_{17}$O—⟨◯⟩(CN)(F)—⟨◯⟩—⟨◯⟩—C$_5$H$_{11}$-n | 18 wt % |
| Dopant 1 | 6.25 wt % |
| Dopant 2 * | 3.75 wt % |

<20 Sc 90 S$_A$ 124 N 133 I

This mixture shows a room temperature Sc phase, with a higher temperature S$_A$ phase which assists alignment in a liquid crystal device. Switching response time (μsec) at various peak voltages with zero volts AC bias at 30° C., and spontaneous polarisation Ps at various temperatures using a 2 μm polyimide aligned cell are tabulated below:

| Peak voltage (v) | Resp. time | Temp (°C.) | P (nC/cm$^2$) |
|---|---|---|---|
| 10 | 205 | 80 | 2.0 |
| 15 | 99 | 70 | 4.5 |
| 20 | 63 | 60 | 6.7 |
| 25 | 46 | 50 | 8.1 |
| 30 | 38 | 40 | 9.3 |
| 35 | 31 | 40 | 9.3 |
| 40 | 27 | 30 | 10.5 |
| 45 | 23 | | |
| 50 | 21 | | |
| 55 | 19 | | |
| 60 | 17 | | |
| 65 | 16 | | |

As 30° C. the cone angle was found to be 23°.

EXAMPLE 10

| | |
|---|---|
| Mixture H2 | 72 wt % |
| n-C$_8$H$_{17}$O—⟨◯⟩(CN)(F)—⟨◯⟩—⟨◯⟩—C$_5$H$_{11}$-n | 18 wt % |
| Dopant 1 | 5.8 wt % |
| Dopant 2 * | 4.2 wt % |

20 Sc 91.5 SA 123.7 N 133.7 I

Switching response times (μsec) at various AC bias voltages, at 30° C. using a 1.9 μm polyimide aligned cell are tabulated below. The cone angle was 23°.

| Peak Voltage (v) | Resp time 0V AC | Resp time 5V AC | Resp time 10V AC |
|---|---|---|---|
| 10 | 1300 | 995 | 530 |
| 15 | 287 | 283 | 280 |
| 20 | 155 | 174 | 219 |
| 25 | 127 | 130 | 192 |
| 30 | 88 | 114 | 213 |
| 35 | 77 | 125 | |
| 40 | 81 | 233 | |
| 45 | 124 | 366 | |
| 50 | 300 | 467 | |

Using a 6 μm polyimide aligned cell the Ps at various temperatures was measured and tabulated below.

| Temp (°C.) | Ps (nC/cm$^2$) |
|---|---|
| 80 | 1.3 |
| 70 | 2.5 |
| 60 | 3.4 |
| 50 | 4.0 |
| 40 | 4.4 |
| 30 | 4.9 |

EXAMPLE 11 (COMPARATIVE)

To illustrate the advantages of use of the terphenyls of the invention in liquid crystal materials two mixtures were prepared containing mixture H2 without a terphenyl of the invention, and proportions of dopants 1 and 2 the same as or very close to those used in the mixtures of examples 9 and 10, identified as mixtures 9A and 10A below.

| | 9A | 10A |
|---|---|---|
| Mixture H2 | 90 wt % | 90 wt % |
| Dopant 1 | 6.25 wt % | 5.63 wt % |
| Dopant 2 | 3.75 wt % | 4.37 wt % |

Their properties were:
9A: 20 Sc* 90.4 SA 109.6 N 133 I
10A: 20 Sc* 93 SA 109.6 N 133 I Hence these two mixtures retain useful Sc phase up to virtually the same temperature as the mixtures of Examples 9 and 10 respectively.

At 30° C. mixtures 9A and 10A showed the following Ps and minimum switching response times (T min) (μl sec) at the voltage (Vmin) and AC bias shown, the corresponding values for mixtures 9 and 10 being given for comparison.

| Mix- | 0V AC | | 5V AC | | 10V AC | | |
|---|---|---|---|---|---|---|---|
| ture | T min | V min | T min | V min | T min | V min | Ps |
| 9 | (17 μsec at 60 V, no V min observed) | | | | | | 10.5 |

| Mix- | 0V AC | | 5V AC | | 10V AC | | |
|------|-------|-------|-------|-------|--------|-------|------|
| ture | T min | V min | T min | V min | T min  | V min | Ps   |
| 9A   | 23    | 50    | 36    | 40    | —      | —     | 8.96 |
| 10   | 77    | 35    | 114   | 30    | 192    | 25    | 4.9  |
| 10A  | 86    | 35    | 149   | 30    | 243    | 20    | 4.24 |

From this stable it can be seen that mixtures 9 and 10, which contain a terphenyl of the invention, have a higher Ps and faster switching times than the corresponding mixtures 9A and 10A which lack such a terphenyl.

An example of the use of a compound of Formula I in a liquid crystal material and device embodying the present invention will now be described with reference to the accompanying drawing, FIG. 12 which is a cross sectional end view of a liquid crystal shutter.

In FIG. 12a liquid crystal cell comprises a layer 1 of liquid crystal material exhibiting a nematic or chiral smectic C phase, between a glass slide 2 having a transparent conducting layer 3 on its surface, eg of tin oxide or indium oxide, and a glass slide 4 having a transparent conducting layer 5 on its surface. The slides 2,4 bearing the layers 3,5 are respectively coated by films 6,7 of a polyimide polymer. Prior to construction of the cell the films 6 and 7 are rubbed with a soft tissue in a given direction the, rubbing directions being arranged parallel upon construction of the cell. A spacer 8 eg of polymethylmethacrylate, separates the crystal material 1 is introduced between the slides 2,4 by filling the space between the slides 2, 4 and spacer 8 and sealing the spacer 8 in a vacuum in a known way, Suitable materials for the layer 1 of liquid crystal are the mixtures of examples 9 and 10 above, with a spacing between the films 6 and 7 of about 2 μm.

We claim:

1. A ferroelectric smectic liquid crystal material being a mixture of compounds wherein at least one of the said compounds is a laterally cyano-substituted terphenyl having the Formula I:

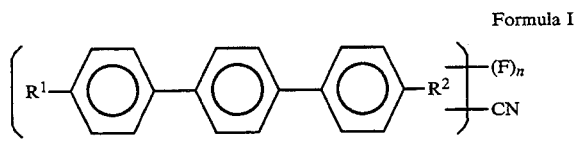

Formula I wherein $R^1$ and $R^2$ are independently selected from hydrogen or $C_{1-15}$ alkyl, alkoxy, or alkyl or alkoxy in which one or more $CH_2$ groups are replaced by O, COO, OOC, CHX, $CX_2$, CH=CX, CX=CH, CX=CX, where X is fluorine or chlorine, CRCN where R is alkyl, or C≡C, or in which a terminal $CH_3$ of the alkyl or alkoxy chain is replaced by $CF_3$, n is 0 or 1, and the F substituents, if present, and the CN substituent are independently located in any of the available substitution positions.

2. The ferroelectric smectic liquid material according to claim 1 wherein one of the compounds of Formula I has the Formula IA:

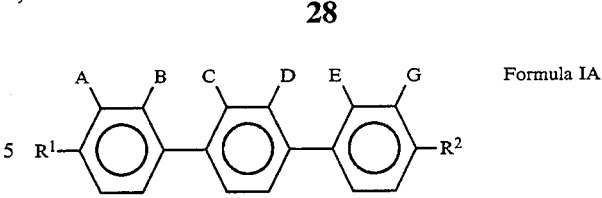

Formula IA wherein $R^1$ and $R^2$ are independently alkyl, alkoxy or alkynyl, and the terphenyl has a subsitution pattern selected from one of the following substitution patterns: (D=CN), (A=CN), (B=F, G=CN), (A=CN, S=F), (n=CN), (C=CN, D=F), (A=F, G=CN), (A=F, E=CN), (B=F, E=CN), (B=F, D=CN), (A=F, D=CN), (A=F, C=CN), (S=F, C=CN), (A=F, S=CN) the remainder lateral substitution positions being occupied by hydrogen.

3. The ferroelectric smectic liquid crystal material according to claim 2 wherein $R^1$ and $R^2$ are independently selected from n-alkyl or n-alkoxy containing 3-12 carbon atoms.

4. The ferroelectric smectic liquid crystal material according to claim 3 wherein one of the compounds of Formula IA has the formula:

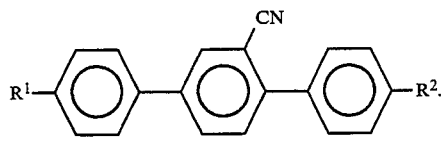

5. The ferroelectric smectic liquid crystal material according to claim 3 wherein one of the compounds of formula IA has the formula:

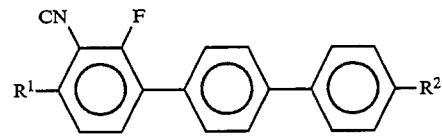

6. The ferroelectric smectic liquid crystal material according to claim 3 wherein one of the compounds of formula has the formula:

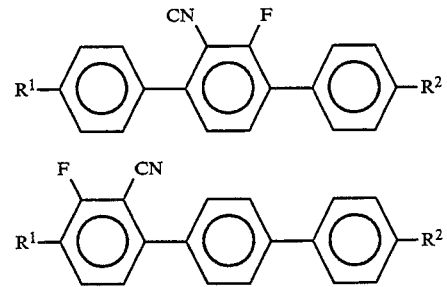

7. The ferroelectric smectic liquid crystal material according to claim 3 wherein one of the compounds of formula has the formula:

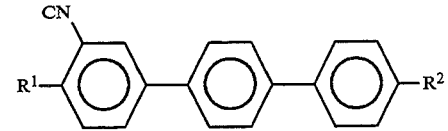

8. The ferroelectric smectic liquid crystal material according to claim 3 wherein one of the compounds of formula IA has the formula:

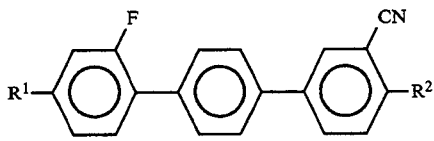

9. The ferroelectric smectic liquid crystal material according to claim 1 wherein said ferroelectric smectic liquid crystal material additionally contains one or more fluorinated terphenyls of the formula:

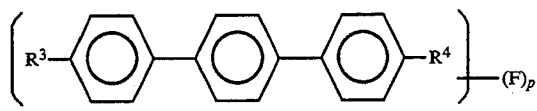

where $R^3$ and $R^4$ are independently selected from hydrogen, alkyl and alkoxy each containing 1–12 carbon atoms, p may be 1 or 2, and the fluoro substituent or substituents may occupy any of the available lateral substitution positions.

10. The ferroelectric smectic liquid crystal material according to claim 9 wherein the fluorinated terphenyl has a formula selected from one of the following:

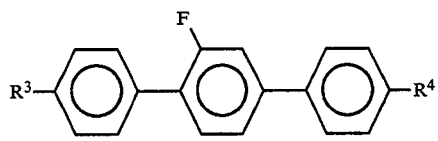

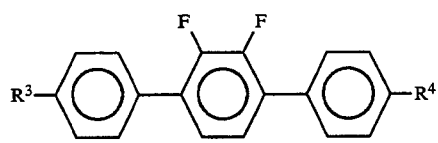

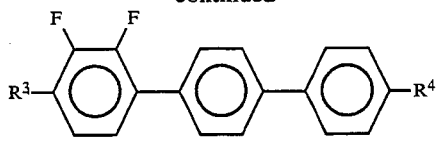

11. The ferroelectric smectic liquid crystal material according to claim 1 where said ferroelectric smectic liquid crystal material additionally contains at least one compound of the formula:

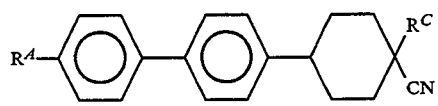

wherein $R^A$ and $R^C$ independently contain 1–12 carbon atoms, $R^A$ is n-alkyl or n-alkoxy, $R^C$ is n-alkyl.

12. The ferroelectric smectic liquid crystal material according to claim 1 where said ferroelectric smectic liquid crystal material additionally contains at least one optically active compound of the formula:

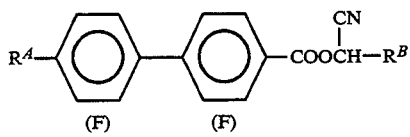

wherein $R^A$ is $C_5$–$C_{12}$ n-alkyl or n-alkoxy, (F) indicates that the adjacent phenyl ring may carry a fluoro substituent, and $R^B$ is $C_1$–$C_4$ n-alkyl, $C_3C_6$ cycloalkyl, or a branched alkyl group of the formula:

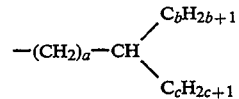

where a is 0 or an integer 1–6 and each of b and c is an integer 1–6.

13. A liquid crystal optical display device comprising two substantially parallel substrates at least one of which is optically transparent and having electrodes on their facing surfaces, and a ferroelectric smectic liquid crystal material according to claim 1.

* * * * *

UNITED STATES PATENT AND TRADEMARK OFFICE
CERTIFICATE OF CORRECTION

PATENT NO. : 5,358,663
DATED : October 25, 1994
INVENTOR(S) : GRAY et al

It is certified that error appears in the above-identified patent and that said letters patent is hereby corrected as shown below:

Claim 2, column 28, line 12, delete "(A=CN, S=F)" insert --(A=CN, B=F);

line 13, delete "(n=CN)" insert --(B-CN)--;

line 15, delete "S=F, C=CN)" insert --(B=F, C=CN)--;

lines 15 -16, delete (A=F, S=CN)" insert --(A=f, B=CN)--.

Claim 6, column 28, line 44, delete "formula has" insert --formula IA has--.

Claim 12, column 30, line 34, delete "$C_3C_6$" insert --$C_3$-$C_6$--.

Signed and Sealed this

Tenth Day of October, 1995

BRUCE LEHMAN

*Attest:*

*Attesting Officer*   *Commissioner of Patents and Trademarks*